United States Patent
Kyushima et al.

(10) Patent No.: US 11,996,434 B2
(45) Date of Patent: May 28, 2024

(54) RADIATION IMAGING DEVICE, PRODUCTION METHOD FOR RADIATION IMAGING DEVICE, AND REPAIR METHOD FOR RADIATION IMAGING DEVICE

(71) Applicant: HAMAMATSU PHOTONICS K.K., Hamamatsu (JP)

(72) Inventors: Ryuji Kyushima, Hamamatsu (JP); Kazuki Fujita, Hamamatsu (JP); Junichi Sawada, Hamamatsu (JP); Takao Aritake, Hamamatsu (JP); Minoru Ichikawa, Hamamatsu (JP); Haruyoshi Okada, Hamamatsu (JP); Seiji Fukamizu, Hamamatsu (JP); Shuhei Namba, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 206 days.

(21) Appl. No.: 17/283,102

(22) PCT Filed: Oct. 9, 2019

(86) PCT No.: PCT/JP2019/039891
§ 371 (c)(1),
(2) Date: Apr. 6, 2021

(87) PCT Pub. No.: WO2020/080233
PCT Pub. Date: Apr. 23, 2020

(65) Prior Publication Data
US 2021/0343778 A1   Nov. 4, 2021

(30) Foreign Application Priority Data
Oct. 18, 2018   (JP) .................................. 2018-196742

(51) Int. Cl.
*H01L 27/146*   (2006.01)
*A61B 6/00*   (2006.01)
(Continued)

(52) U.S. Cl.
CPC .......... *H01L 27/14658* (2013.01); *A61B 6/42* (2013.01); *A61B 6/44* (2013.01); *H01L 27/14603* (2013.01); *H04N 25/70* (2023.01)

(58) Field of Classification Search
None
See application file for complete search history.

(56) References Cited

U.S. PATENT DOCUMENTS

| | | | |
|---|---|---|---|
| 2005/0056789 A1 | 3/2005 | Spahn et al. | |
| 2006/0108683 A1* | 5/2006 | Takeda | H01L 27/14663 257/723 |

(Continued)

FOREIGN PATENT DOCUMENTS

| | | |
|---|---|---|
| CN | 101507610 A | 8/2009 |
| CN | 101507611 A | 8/2009 |

(Continued)

OTHER PUBLICATIONS

International Preliminary Report on Patentability dated Apr. 29, 2021 for PCT/JP2019/039891.

*Primary Examiner* — Edwin C Gunberg
(74) *Attorney, Agent, or Firm* — Faegre Drinker Biddle & Reath LLP

(57) ABSTRACT

A radiation imaging device according to one embodiment includes a radiation detection panel having a first surface on which a detection region is formed and an electrode pad is formed outside the detection region, and a second surface on a side opposite to the first surface, a base substrate having a support surface configured to face the second surface of the radiation detection panel and configured to support the radiation detection panel, and a flexible circuit substrate connected to the electrode pad via a connecting member, wherein an end portion of the base substrate is located further inward than an inner end portion of the connection region in which the electrode pad, the connecting member, and the flexible circuit substrate overlap each other when seen in an Z direction orthogonal to the support surface.

16 Claims, 14 Drawing Sheets

(51) Int. Cl.
    *A61B 6/42*           (2024.01)
    *H04N 25/70*        (2023.01)

(56) References Cited

U.S. PATENT DOCUMENTS

| | | | |
|---|---|---|---|
| 2009/0061233 A1* | 3/2009 | Yaegashi | B32B 37/12 |
| | | | 156/308.2 |
| 2012/0256091 A1 | 10/2012 | Nakahashi | |
| 2014/0027636 A1* | 1/2014 | Watano | G01T 1/16 |
| | | | 250/336.1 |
| 2016/0181308 A1 | 6/2016 | Ichimura et al. | |
| 2016/0252629 A1 | 9/2016 | Hiratsuka et al. | |
| 2016/0282482 A1* | 9/2016 | Kobayashi | G01T 1/2018 |
| 2016/0302302 A1* | 10/2016 | Yachi | H05K 1/0216 |

FOREIGN PATENT DOCUMENTS

| | | |
|---|---|---|
| CN | 105403906 A | 3/2016 |
| CN | 105997111 A | 10/2016 |
| CN | 106054234 A | 10/2016 |
| JP | 2010-145349 A | 7/2010 |
| JP | 2016-161292 A | 9/2016 |
| JP | 2016-200544 A | 12/2016 |
| JP | 2018-107343 A | 7/2018 |
| WO | WO 2018/123189 A1 | 7/2018 |

* cited by examiner

*Fig.1*
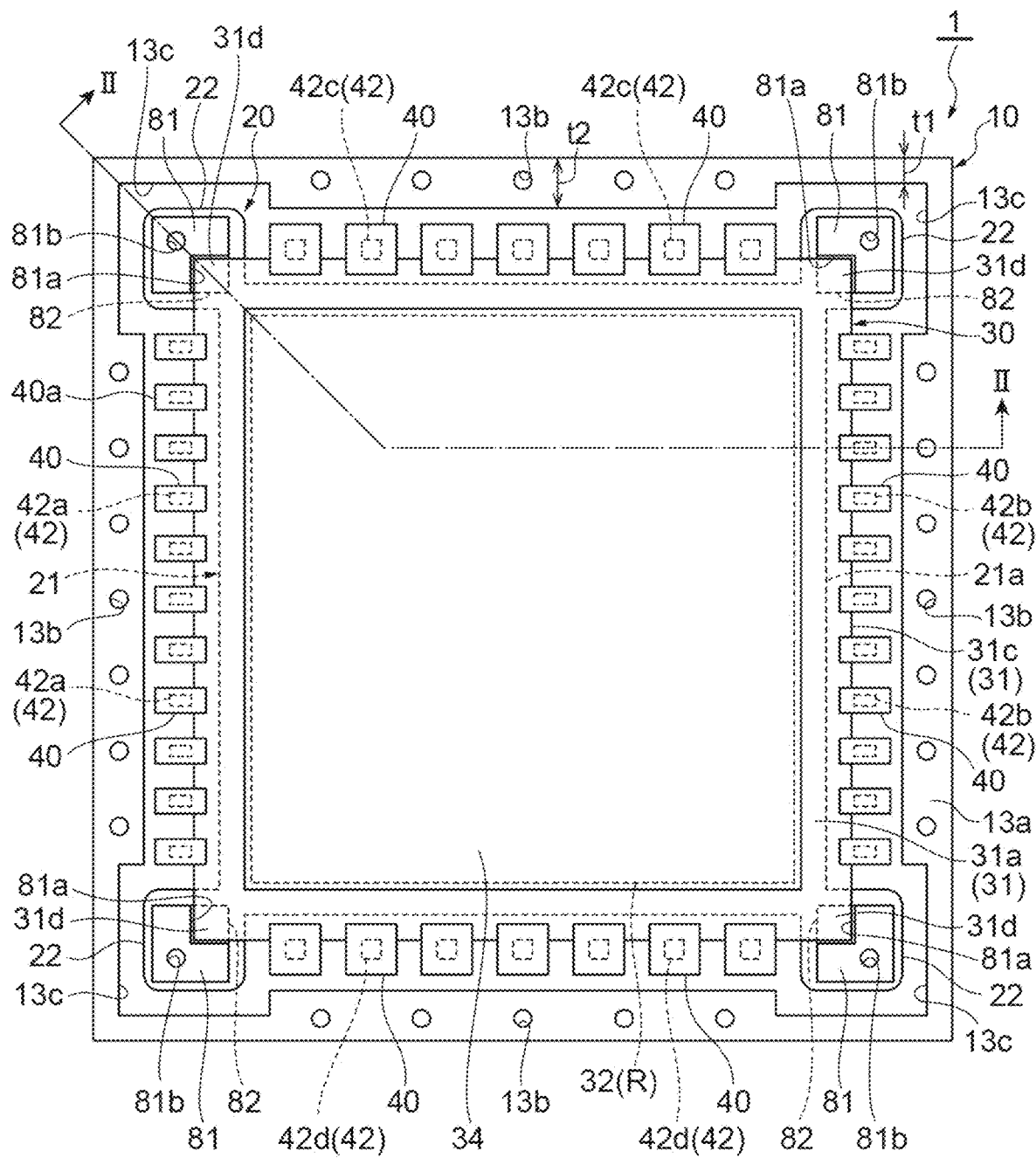
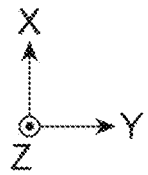

*Fig.7*
(A)
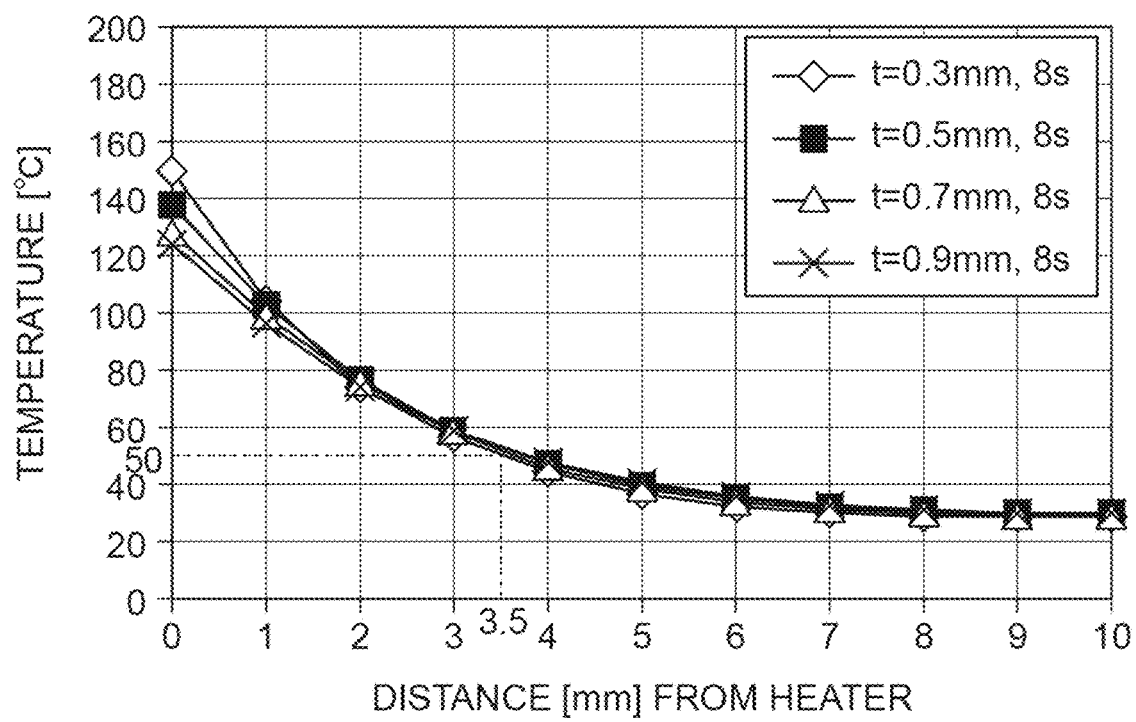
(B)
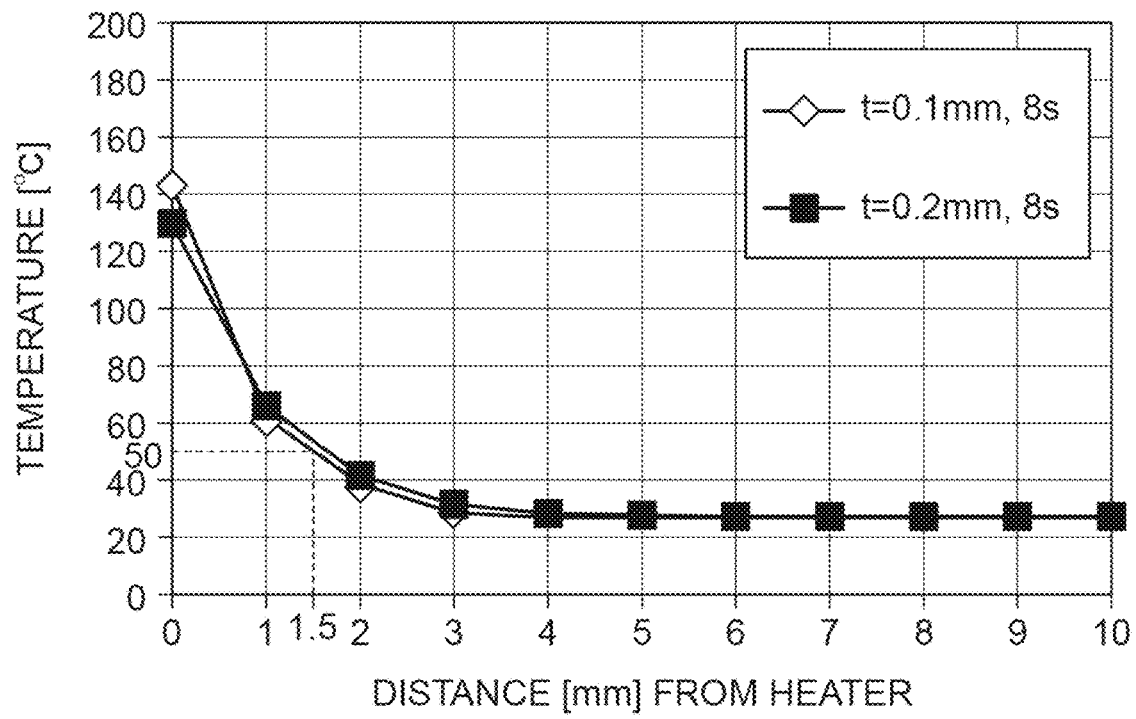

Fig.8
(A)
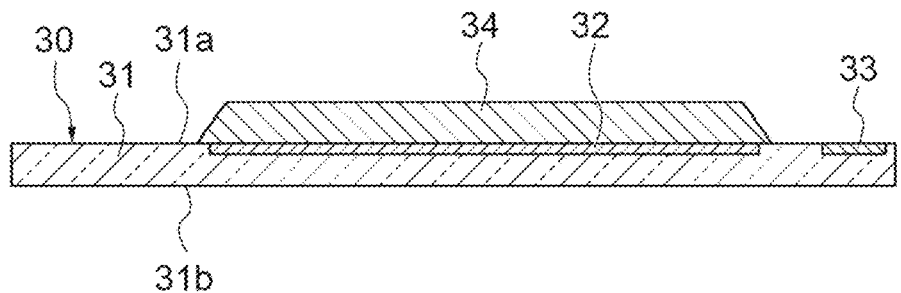
(B)
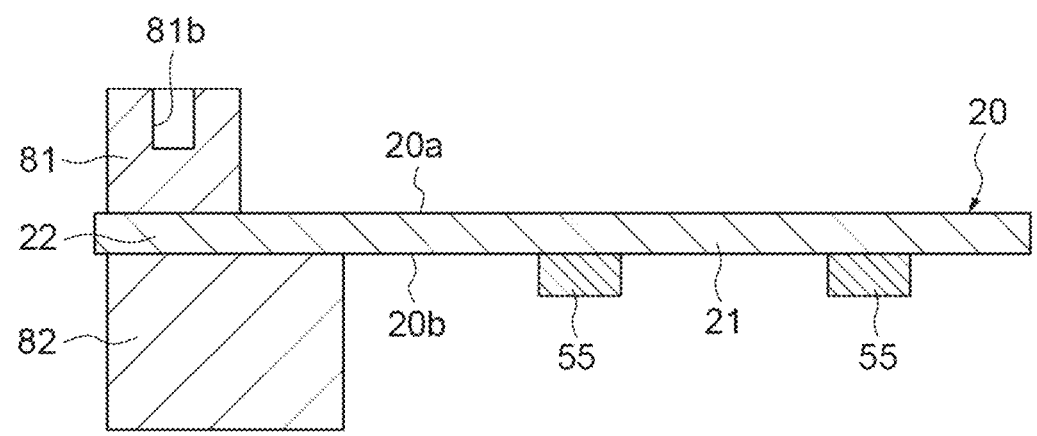
(C)
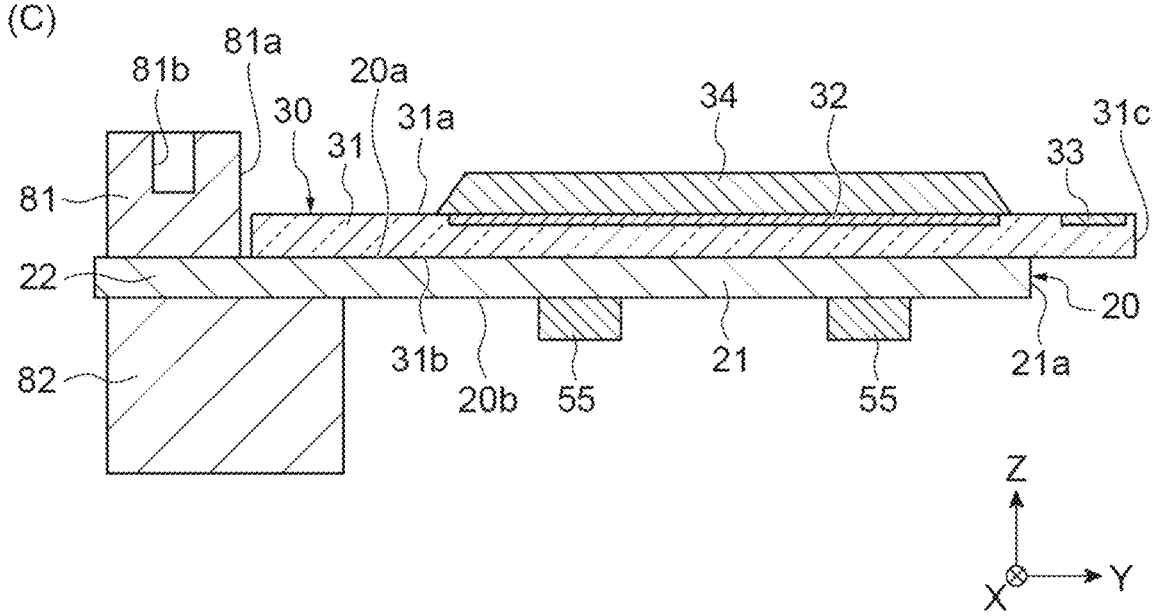

RADIATION IMAGING DEVICE, PRODUCTION METHOD FOR RADIATION IMAGING DEVICE, AND REPAIR METHOD FOR RADIATION IMAGING DEVICE

TECHNICAL FIELD

The disclosure relates to a radiation imaging device, a method of manufacturing the radiation imaging device, and a repair method of the radiation imaging device.

BACKGROUND ART

Patent Document 1 describes an X-ray detection device. This X-ray detection device includes a support member, an X-ray detection panel fixed on the support member, and a flexible circuit substrate on which an external IC is mounted. One end of the flexible circuit substrate is disposed via an adhesive member (an anisotropic conductive adhesive) on an electrode pad (a charge extraction part) disposed at a peripheral edge portion of the X-ray detection panel.

CITATION LIST

Patent Document

[Patent Document 1] Japanese Unexamined Patent Publication No. 2010-145349

SUMMARY OF INVENTION

Technical Problem

When one end of the flexible circuit substrate is connected to the electrode pad as described above, a process in which the adhesive member is thermocompression bonded by sandwiching the flexible circuit substrate, the adhesive member, and the X-ray detection panel between a pair of heater members and heating them is performed. Further, when the flexible circuit substrate is repaired (replaced, and the like), the above-described thermocompression bonding is performed when the flexible circuit substrate (or a spare part, and the like) after the repair is mounted again. However, when a back surface (a surface on the side opposite to the surface on which the electrode pad is provided) of the X-ray detection panel is completely covered with the support member as in the X-ray detection device, the heater member disposed on the X-ray detection panel side and the support member interfere with each other. Therefore, in the configuration of the X-ray detection device, when the flexible circuit substrate is repaired, it is necessary to remove the X-ray detection panel from the support member. Therefore, there is room for improvement in the X-ray detection device from the viewpoint of workability.

Further, when an end portion of the support member is located further outward than an end portion of the X-ray detection panel when seen in a direction orthogonal to the X-ray detection panel (an X-ray incident direction), it is necessary to route the flexible circuit substrate further outward than the end portion of the support member. The flexible circuit substrate becomes longer by an amount of such routing that is required, and noise is easily added to a signal transmitted through the flexible circuit substrate.

One aspect of the disclosure is to provide a radiation imaging device, a method of manufacturing the radiation imaging device, and a repair method of the radiation imaging device which are capable of facilitating repair work of a flexible circuit substrate and curbing noise in a signal transmitted through the flexible circuit substrate.

Solution to Problem

A radiation imaging device according to an aspect of the disclosure includes a radiation detection panel having a first surface on which a detection region for detecting radiation is formed and an electrode pad is formed outside the detection region, and a second surface on a side opposite to the first surface, a base substrate having a support surface configured to face the second surface of the radiation detection panel and configured to support the radiation detection panel, and a flexible circuit substrate connected to the electrode pad via a connecting member, wherein an end portion of the base substrate is located further inward than an inner end portion of the connection region in which the electrode pad, the connecting member, and the flexible circuit substrate overlap each other when seen in a first direction orthogonal to the support surface.

In the radiation imaging device, when the flexible circuit substrate is connected to the electrode pad, it may be necessary to heat the flexible circuit substrate, the connecting member, and radiation detection panel with a heater from both sides in the first direction. On the other hand, in the radiation imaging device, the end portion of the base substrate is located further inward than the inner end portion of the connection region when seen in the first direction. Thus, it is possible to avoid interference between the heater disposed on the second surface side of the radiation detection panel and the base substrate. Therefore, when it becomes necessary to repair (replace, or the like) the flexible circuit substrate, the flexible circuit substrate can be repaired without removing the radiation detection panel from the base substrate. Therefore, according to the radiation imaging device, a repair work of the flexible circuit substrate can be facilitated. Further, when the end portion of the base substrate is located further outward the end portion of the radiation detection panel when seen in the first direction, it is necessary to route the flexible circuit substrate further outward than the end portion of the base substrate. The flexible circuit substrate becomes longer by an amount that such routing is required, and noise is easily added to a signal transmitted through the flexible circuit substrate. On the other hand, in the radiation imaging device, the end portion of the base substrate is located further inward than the inner end portion of the connection region (that is, further inward than the end portion of the radiation detection panel) when seen in the first direction. Therefore, it is not necessary to route the flexible circuit substrate as described above, and the overall length of the flexible circuit substrate can be shortened. As a result, it is possible to curb noise in the signal transmitted through the flexible circuit substrate.

The radiation detection panel may be formed in a rectangular shape when seen in the first direction, one or more of the connection regions may be formed on at least one side portion of the radiation detection panel, and the end portion of the base substrate may be located further inward than inner end portions of all the connection regions formed on the at least one side portion when seen in the first direction. With such a configuration, a position of an outer end portion of the flexible circuit substrate connected to the connection region on at least one side portion when seen in the first direction can be brought closer to the end portion of the radiation detection panel without interfering with the end portion of the base substrate. That is, the outer end portion of the flexible circuit substrate on the at least one side portion can be located as inward as possible. Thus, a size of the device can be reduced. For example, when the base substrate, the radiation detection panel, and the like are accommodated in a housing, a size of the housing can be reduced.

The radiation imaging device may further include a conversion part disposed on the first surface to constitute the detection region and configured to convert radiation into light or electric charge, the end portion of the base substrate may be located further outward than the detection region when seen in the first direction, and a distance between the inner end portion of the connection region and the end portion of the base substrate in a second direction orthogonal to the first direction may be 1 mm or more. The conversion part which converts radiation into light or electric charge often has a property in which it is sensitive to heat. With such a configuration, when the flexible circuit substrate is connected to the electrode pad, the distance between the heater which heats the connecting member and the conversion part can be secured at a certain level or more (at least 1 mm or more). As a result, an adverse effect of the heat from the heater on the conversion part can be curbed.

The conversion part may be a scintillator which converts radiation into light. A moisture-proof film having a moisture-proof property may be provided on the scintillator. Such a moisture-proof film has a property in which it is particularly sensitive to heat. With such a configuration, it is possible to curb an adverse effect of the heat from the heater on the scintillator (including the moisture-proof film) having such a particularly heat-sensitive property.

The base substrate may have a protruding portion which protrudes further outward than the radiation detection panel at a position at which the base substrate does not overlap the flexible circuit substrate when seen in the first direction. With such a configuration, since the protruding portion can be used as a gripping portion in a state in which the radiation detection panel is supported on the base substrate, handleability at the time of manufacturing or repairing the radiation imaging device can be improved.

A first extending portion which extends in the first direction may be provided on the support surface of the protruding portion. For example, the first extending portion may be a positioning member which positions the radiation detection panel. With such a configuration, since the first extending portion makes it possible to easily position the radiation detection panel with respect to the support surface of the base substrate, assembly workability can be improved.

The radiation imaging device may further include a housing configured to accommodate the radiation detection panel, the base substrate, and the flexible circuit substrate, the housing may have a first wall portion which faces the first surface and a second wall portion which faces the second surface, and the base substrate may be supported on the first wall portion via the first extending portion. With such a configuration, since the base substrate (the protruding portion) is supported on the housing (a first wall portion) via the first extending portion, the base substrate can be stably supported with respect to the housing.

A second extending portion which is disposed at a position at which the second extending portion faces the first extending portion with the protruding portion interposed therebetween and extends in the first direction may be provided on a surface of the protruding portion on a side opposite to the support surface, and the base substrate may be supported on the second wall portion via the second extending portion. With such a configuration, the base substrate (the protruding portion) is sandwiched by parts of the housing (the first wall portion and the second wall portion) which faces each other via the first extending portion and the second extending portion. Thus, the base substrate can be supported more stably with respect to the housing. Here, as a method of supporting the base substrate with respect to the housing, for example, there is a method of supporting a back surface of the base substrate (a surface on the side opposite to the support surface) on the second wall portion via a columnar support member. With such a configuration, the base substrate is supported on the housing via the first extending portion and the second extending portion. Therefore, when the above-described supporting method is used in combination, the number of support members provided on the back surface of the base substrate can be reduced. Thus, it is possible to make it difficult for an impact from the outside (particularly the second wall portion) to be transmitted to the back surface of the base substrate. As a result, it is possible to reduce the impact on the radiation detection panel supported on the base substrate.

The first extending portion and the second extending portion may be formed separately from the base substrate. With such a configuration, warpage of the base substrate can be reduced as compared with a case in which the base substrate is integrally formed with at least one of the first extending portion and the second extending portion.

A method of manufacturing a radiation imaging device according to an aspect of the disclosure includes a step of preparing a radiation detection panel having a first surface on which a detection region for detecting radiation is formed and an electrode pad is formed outside the detection region, and a second surface on a side opposite to the first surface, a step of supporting the second surface of the radiation detection panel on a support surface of a base substrate, and a step of connecting a flexible circuit substrate to the electrode pad via a connecting member, wherein, in the supporting step, the base substrate is disposed with respect to the radiation detection panel so that an end portion of the base substrate is located further inward than an inner end portion of a connection region in which the electrode pad, the connecting member, and the flexible circuit substrate will overlap each other when seen in a first direction orthogonal to the support surface, and in the connecting step, the connecting member is heated by a first heater disposed on a side opposite to the connecting member with the flexible circuit substrate interposed therebetween and a second heater disposed on a side opposite to the connecting member with the radiation detection panel interposed therebetween.

According to the manufacturing method, in the supporting step, it is possible to thermocompression bond the flexible circuit substrate, the connecting member, and the radiation detection panel between the first heater and the second heater by disposing the base substrate not to overlap the connection region. That is, when the flexible circuit substrate and the electrode pad are connected, it is possible to prevent the second heater and the base substrate from interfering with each other. Thus, the flexible circuit substrate can be connected to the radiation detection panel in a state in which the radiation detection panel is stably supported by the base substrate. Further, a sufficient connection strength can be ensured at a lower heating temperature (a heater temperature) by heating from both sides (the flexible circuit substrate side and the radiation detection panel side) of the connecting member with the first heater and the second heater, as compared with a case of heating from one side of the connecting member. Therefore, according to the manufacturing method, it is possible to secure the connection strength while an adverse effect of the heat during heating on the radiation detection panel and the like is curbed.

A repair method of the radiation imaging device according to an aspect of the disclosure includes a step of removing a first flexible circuit substrate from the electrode pad in a state in which the radiation detection panel is supported on the base substrate, and a step of connecting a second flexible circuit substrate to the electrode pad via the connecting member by heating the connecting member with a first heater disposed on a side opposite to the connecting member with the second flexible circuit substrate interposed therebetween and a second heater disposed on a side opposite to the connecting member with the radiation detection panel interposed therebetween in the state in which the radiation detection panel is supported on the base substrate.

According to the repair method, the flexible circuit substrate can be repaired (the removing step and the connecting step) without removing the radiation detection panel from the base substrate by disposing the base substrate not to overlap the connection region.

Advantageous Effects of Invention

According to the aspect of the disclosure, it is possible to provide a radiation imaging device, a method of manufacturing the radiation imaging device, and a repair method of the radiation imaging device which are capable of facilitating a repair work of a flexible circuit substrate and curbing noise in a signal transmitted through the flexible circuit substrate.

BRIEF DESCRIPTION OF DRAWINGS

FIG. 1 is a plan view of a radiation imaging device of one embodiment.

FIG. 7 is a diagram showing a relationship between a distance from a heater and a temperature in the radiation detection panel.

FIG. 8 is a diagram showing an example of a manufacturing process of the radiation imaging device.

DESCRIPTION OF EMBODIMENTS

Figure 2:
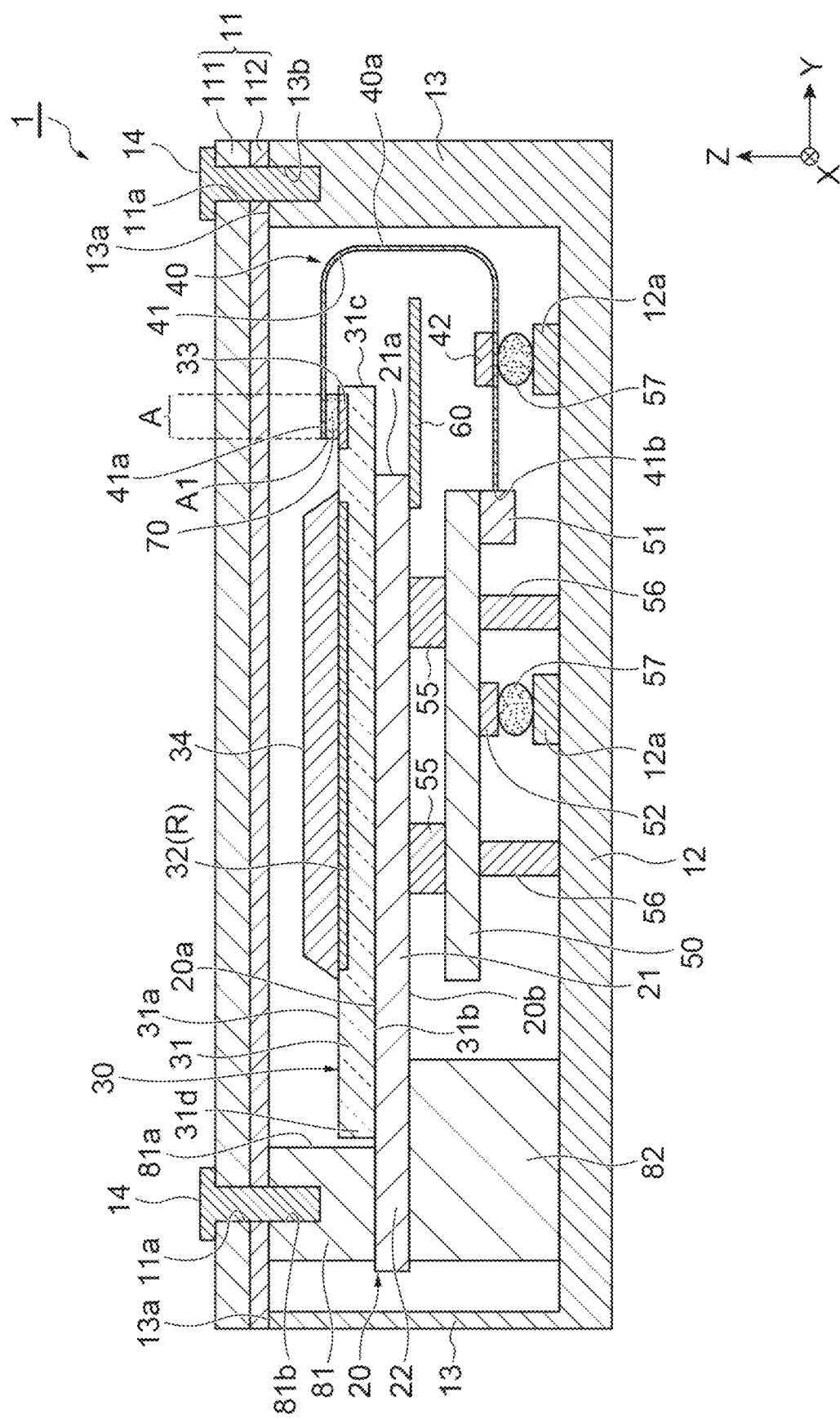
FIG. 2 is a cross-sectional view taken along line II-II of FIG. 1.

Hereinafter, embodiments of the disclosure will be described in detail with reference to the accompanying drawings. In the description of the drawings, the same reference numerals are used for the same or equivalent elements, and duplicate description thereof will be omitted. The disclosure is not limited to these examples, but is shown by the scope of claims and is intended to include all modifications within the meaning and scope equivalent to the scope of claims. For ease of understanding, XYZ orthogonal coordinate systems are shown in FIGS. 1 to 4, 6 and 8 to 11.

FIG. 1 is a plan view of a radiation imaging device 1 according to an embodiment of the disclosure. FIG. 2 is a cross-sectional view taken along line II-II of FIG. 1. However, in FIG. 1, a top wall 11 and a screw member 14 are not shown. The radiation imaging device 1 is, for example, a large-area flat panel sensor used in a medical X-ray imaging system. As shown in FIGS. 1 and 2, the radiation imaging device 1 includes a housing 10, a base substrate 20, a radiation detection panel 30, a flexible circuit substrate 40, a control substrate 50, and a radiation shielding member 60.

The housing 10 is a hollow container having a substantially rectangular parallelepiped shape. The housing 10 has a top wall 11 (a first wall portion), a bottom wall 12 (a second wall portion), and a side wall 13 (a third wall portion). The top wall 11 and the bottom wall 12 are each formed in a rectangular plate shape which extends along an XY plane, and face each other. The side wall 13 extends along an XZ plane or an YZ plane, and connects an edge portion of the top wall 11 with an edge portion of the bottom wall 12. That is, the side wall 13 is formed in a rectangular ring shape when seen in a Z direction. The housing 10 accommodates the base substrate 20, the radiation detection panel 30, the flexible circuit substrate 40, the control substrate 50, and the radiation shielding member 60.

The top wall 11 is configured of a member which allows radiation (for example, X-rays) to be detected by the radiation imaging device 1 to be transmitted to the inside of the housing 10. The top wall 11 guides the radiation incident in the Z direction to the inside of the housing 10. That is, the Z direction is an incident direction of the radiation to be detected. In the embodiment, the top wall 11 has a two-layer structure. Specifically, the top wall 11 includes a carbon fiber plate 111 provided on the side (the outer side) on which the radiation is incident, and a shield member 112 provided on an inner surface of the carbon fiber plate 111 to shield electromagnetic waves. The shield member 112 is, for example, an aluminum shield formed by adhering an aluminum foil to the inner surface of the carbon fiber plate 111.

The bottom wall 12 and the side wall 13 are formed of a metal material (for example, iron or the like) which blocks radiation. An upper surface 13a of the side wall 13 is in surface contact with the shield member 112 and is electrically connected to the shield member 112. Thus, electromagnetic waves directed from the outside of the housing 10 to the inside of the housing 10 are shielded. Further, a plurality of screw holes 13b are provided in the upper surface 13a of the side wall 13. The screw member 14 is inserted through a through hole 11a provided in the top wall 11 and screwed into the screw hole 13b. Accordingly, the top wall 11 is fixed to the side wall 13.

The base substrate 20 is a member which supports the radiation detection panel 30, the control substrate 50, and the radiation shielding member 60. The base substrate 20 is made of, for example, a metal such as iron, aluminum, stainless steel, a tungsten alloy, copper tungsten or the like. As an example, in the embodiment, the base substrate 20 is made of relatively lightweight aluminum. The base substrate 20 has a support surface 20a and a back surface 20b on the side opposite to the support surface 20a. The support surface 20a is a surface which faces the top wall 11, and the back surface 20b is a surface which faces the bottom wall 12. The support surface 20a supports a substrate 31 of the radiation detection panel 30. The control substrate 50 is fixed to the back surface 20b via, for example, one or more support members 55 formed in a columnar shape which extends in the Z direction.

The radiation detection panel 30 has the substrate 31 formed in a rectangular plate shape. The substrate 31 has a first surface 31a on which a light receiving part 32 (a light receiving surface) is formed, and a second surface 31b on the side opposite to the first surface 31a. The first surface 31a is a surface which faces the top wall 11, and the second surface 31b is a surface which faces the bottom wall 12. A scintillator 34 (a conversion part) is disposed on the light receiving part 32. The scintillator 34 is formed by, for example, depositing a scintillator material containing CsI as a main component on the light receiving part 32. The scintillator 34 converts radiation incident through the top wall 11 into light. Specifically, the scintillator 34 outputs scintillation light having an intensity corresponding to an incident intensity of radiation to the light receiving part 32. Thus, a region on the first surface 31a in which the light receiving part 32 is formed serves as a detection region R for detecting radiation. The detection region R has, for example, a light receiving area (for example, 40 cm×30 cm) having a side of about 30 cm to 40 cm.

The substrate 31 is, for example, a transparent glass substrate. The substrate 31 is fixed to the base substrate 20 by the second surface 31b of the substrate 31 being fixed to the support surface 20a of the base substrate 20. For example, the second surface 31b of the substrate 31 is fixed to the support surface 20a of the base substrate 20 via an adhesive member G (refer to FIG. 6) such as double-sided tape. When seen in the Z direction, at least the region in which the light receiving part 32 and the scintillator 34 are disposed is included in the support surface 20a. Further, the adhesive member G (refer to FIG. 6) is provided at least in a region overlapping the light receiving part 32 when seen in the Z direction. Further, an outer end portion of the adhesive member G is located further inward than an end portion (an end portion 21a described later) of the base substrate 20 when seen in the Z direction. On the first surface 31a of the substrate 31, a plurality of electrode pads 33 are formed on the outside of the detection region R. The plurality of electrode pads 33 are electrically connected to pixels $P_{m,n}$ (refer to FIG. 3) formed in the light receiving part 32 via a wire (a reading wire and a row selection wire) described later. In the embodiment, as an example, 22 (11×2 sides) electrode pads 33 are formed on a peripheral edge portion of the substrate 31 in an X direction. Further, 14 (7×2 sides) electrode pads 33 are formed on the peripheral edge portion of the substrate 31 in a Y direction.

The flexible circuit substrate 40 is a circuit member electrically connected to the electrode pads 33. The flexible circuit substrate 40 includes a flexible substrate 41 which can be deformed by bending or the like, and an IC chip 42 mounted on the flexible substrate 41. The flexible substrate 41 has, for example, a structure in which a circuit pattern made of a conductor foil (for example, copper or the like) is formed on a thin film insulator (for example, polyimide or the like). One end portion 41a of the flexible substrate 41 is connected to the electrode pads 33 via a connecting member 70. The connecting member 70 is a member which generates an adhesive force by thermocompression bonding, and is an anisotropic conductive material such as an anisotropic conductive film (ACF) or anisotropic conductive paste (ACP). The other end portion 41b of the flexible substrate 41 is connected to the control substrate 50 (a connector 51).

The control substrate 50 includes a circuit which controls an operation of the IC chip 42 (for example, an operation of vertical shift registers 42a and 42b and signal connection parts 42c and 42d which will be described later) and supplies electric power to the IC chip 42. Specifically, for example, electric power is supplied to the control substrate 50 from an external power source (not shown) disposed on the outside of the housing 10 (for example, the outside of the bottom wall 12), and the electric power is supplied to the IC chip 42 via the control substrate 50. The external power source may be disposed inside the housing 10 (for example, a space between the control substrate 50 and the bottom wall 12). However, from the viewpoint of curbing generation of measurement noise caused by the external power source, it is preferable that the external power source is disposed outside the housing 10. The control substrate 50 is fixed to the back surface 20b of the base substrate 20 via one or more of the above-described support members 55. Further, the control substrate 50 is also fixed to the bottom wall 12 via a support member 56 similar to the support member 55. The support member 55 and the support member 56 may be integrally formed as a columnar member which supports the control substrate 50 while passing through the control substrate 50 in the Z direction. Such a columnar member serves as a member which supports the base substrate 20 with respect to the bottom wall 12 and supports the control substrate 50 with respect to the bottom wall 12 and the base substrate 20.

Here, the IC chip 42 mounted on the flexible circuit substrate 40 and an AD converter 52 mounted on the control substrate 50 are parts (heat generating members) which are particularly likely to generate heat. Further, when heat from the IC chip 42 or the AD converter 52 is transferred to the radiation detection panel 30, noise may be generated in an image acquired by the light receiving part 32. Therefore, in the embodiment, a heat sink member 57 is disposed between each of the IC chip 42 and the AD converter 52 and the bottom wall 12 to efficiently release the heat generated from the IC chip 42 and the AD converter 52 to the bottom wall 12 of the housing 10. The heat sink member 57 is, for example, a gel sheet or the like of which a main material is silicone or the like. As shown in FIG. 2, when a distance between the IC chip 42 or the AD converter 52 and the bottom wall 12 is large, a projection 12a which protrudes toward the top wall 11 side may be provided on a portion of the inner surface of the bottom wall 12 which overlaps the IC chip 42 or the AD converter 52 when seen in the Z direction. According to such a projection 12a, the heat generated from the IC chip 42 or the AD converter 52 can be appropriately released to the bottom wall 12 via the heat sink member 57 and the projection 12a. Further, it is possible to utilize a portion in which the projection 12a is not provided as a space for accommodating various parts and the like by partially raising the inner surface of the bottom wall 12.

The control substrate 50 overlaps the scintillator 34 and the base substrate 20 when seen in the Z direction. That is, most of the radiation incident from the top wall 11 and directed to the control substrate 50 is shielded by the scintillator 34 and the base substrate 20. On the other hand, as in the embodiment, the IC chip 42 mounted on the flexible circuit substrate 40 may be disposed at a position at which it does not overlap the scintillator 34 and the base substrate 20 when seen in the Z direction. That is, the radiation incident from the top wall 11 and directed to the IC chip 42 may not be shielded by the scintillator 34 and the base substrate 20. In this case, when no measures are taken, the IC chip 42 may be damaged by the radiation, and a malfunction of the IC chip 42 or the like may be caused. Therefore, in the embodiment, the radiation shielding member 60 is provided to shield the radiation incident from the top wall 11 and directed to the IC chip 42.

The radiation shielding member 60 is made of a material having high X-ray shielding ability such as lead and tungsten. In the embodiment, as an example, the radiation shielding member 60 is formed in a strip shape and is provided at an edge portion of the back surface 20b of the base substrate 20. A part of the radiation shielding member 60 protrudes to the outside of the base substrate 20 to overlap the IC chip 42 when seen in the Z direction. The radiation shielding member 60 may be provided for each of the IC chips 42, or one radiation shielding member 60 (that is, a member formed in a size which overlaps the plurality of IC chips when seen in the Z direction) may be provided for a plurality of IC chips 42 adjacent to each other. In the embodiment, a weight of the radiation imaging device 1 is reduced by the base substrate 20 being made of relatively lightweight aluminum and the radiation shielding member 60 made of a relatively heavy material as described above being provided in part of a place in which radiation needs to be shielded.

The base substrate 20 includes a main body 21 which is formed in a rectangular shape when seen in the Z direction (a first direction) orthogonal to the support surface 20a, and a protruding portion 22 which is formed at each of corner portions (four corners) of the main body 21 and protrudes to the outside of the main body 21. In the embodiment, as an example, the protruding portion 22 is formed in a substantially rectangular shape of which corners are chamfered when seen in the Z direction. Further, the main body 21 and the protruding portion 22 are integrally formed, and a thickness (a plate thickness) of the protruding portion 22 is the same as a thickness of the main body 21. That is, the base substrate 20 is configured as a single plate having a substantially uniform thickness.

When seen in the Z direction, an end portion of the base substrate 20 corresponding to a portion in which the flexible circuit substrate 40 is connected to the electrode pad 33 is located further inward (on the detection region R side) than an end portion of the radiation detection panel 30 (that is, an end portion 31c of the substrate 31). Specifically, the main body 21 is formed in a rectangular shape smaller than the substrate 31 when seen in the Z direction, and the end portion 21a of the main body 21 is located further inward than the end portion 31c of the substrate 31. That is, the end portion of the base substrate 20 (that is, the end portion 21a of the main body 21) corresponding to each of side portions (portions in which the electrode pad 33 is formed) of the radiation detection panel 30 is located further inward than the end portion 31c of the substrate 31. Furthermore, in the embodiment, the base substrate 20 is formed not to overlap a connection region A in which the electrode pad 33, the connecting member 70, and the flexible circuit substrate 40 (the one end portion 41a of the flexible substrate 41) overlap each other when seen in the Z direction. That is, the end portion 21a of the main body 21 is located further inward than an inner end portion A1 of the connection region A. Thus, a configuration in which the base substrate 20 does not overlap the connection region A (36 connection regions A in the embodiment) when seen in the Z direction is realized.

The protruding portion 22 protrudes further outward than the radiation detection panel 30 at a position (as an example in the embodiment, the corner portion of the main body 21) at which it does not overlap the flexible circuit substrate 40 when seen in the Z direction. That is, when seen in the Z direction, the protruding portion 22 protrudes further outward than the substrate 31. In the embodiment, the protruding portion 22 protrudes further outward than an end portion (a bent portion which is a portion farthest from the end portion 31c of the substrate 31 in a direction parallel to the XY plane) of the flexible substrate 41 when seen in the Z direction.

A first extending portion 81 which extends in the Z direction is provided in the support surface 20a of the protruding portion 22. As an example in the embodiment, the first extending portion 81 is made of aluminum. However, the first extending portion 81 may be formed of other materials. For example, the material of the first extending portion 81 may be a metal other than aluminum such as iron, engineering plastics such as polyacetal (POM) and polyetheretherketone (PEEK), and the like. The first extending portion 81 is fixed to the protruding portion 22 via, for example, a fixing member (for example, a screw or the like) which is not shown. In the embodiment, the first extending portion 81 is a columnar member which extends in the Z direction and serves as a positioning member for positioning the radiation detection panel 30 (that is, the substrate 31). Specifically, the first extending portion 81 has a guide groove 81a which extends in the Z direction to accommodate a corner portion 31d of the substrate 31. The guide groove 81a is formed in an L shape to match a shape of the corner portion 31d of the substrate 31 when seen in the Z direction. That is, the first extending portion 81 has a shape in which a part (a square columnar portion corresponding to a space formed by the guide groove 81a) of a square columnar member (a member having the same shape as a second extending portion 82 which will be described later) is cut out. In the embodiment, such a first extending portion 81 is provided corresponding to each of the four corners of the substrate 31. That is, the substrate 31 can be positioned by disposing each of the corner portions 31d of the substrate 31 inside the guide groove 81a of each of the first extending portions 81.

The first extending portion 81 is supported by the top wall 11. In the embodiment, a screw hole 81b is formed in the surface of the first extending portion 81 on the top wall 11 side. Then, the screw member 14 is inserted through the through hole 11a provided in the top wall 11 and screwed into the screw hole 81b. In this way, the first extending portion 81 is supported by the top wall 11 and is also supported by the protruding portion 22. That is, the base substrate 20 is supported by the top wall 11 via the first extending portion 81. In the embodiment, the base substrate 20 (the protruding portion 22) is firmly fixed to the top wall 11 via the first extending portion 81 by screwing.

The second extending portion 82 which is disposed at a position at which it faces the first extending portion 81 with the protruding portion 22 interposed therebetween and extends in the Z direction is provided in the back surface 20b of the protruding portion 22. As an example in the embodiment, the second extending portion 82 is made of aluminum. However, the same material as the above-described material of the first extending portion 81 can be used as the material of the second extending portion 82. The second extending portion 82 is supported by the protruding portion 22 via, for example, a fixing member (for example, a screw or the like) which is not shown. The first extending portion 81 and the second extending portion 82 may be fixed to the protruding portion 22 by being screwed from the first extending portion 81 side or the second extending portion 82 side using a common screw, or may be fixed to the protruding portion 22 by being individually screwed using different screws. Further, the second extending portion 82 is supported by the bottom wall 12 by the same fixing means as that of the first extending portion 81. For example, a screw hole (not shown) is formed in a surface of the second extending portion 82 on the bottom wall 12 side, and a screw member (not shown) is inserted through a through hole (not shown) provided in the bottom wall 12 and screwed into the screw hole. In this way, the second extending portion 82 is supported by the protruding portion 22 and the bottom wall 12. That is, the base substrate 20 is supported by the bottom wall 12 via the second extending portion 82. In the embodiment, the base substrate 20 (the protruding portion 22) is firmly fixed to the bottom wall 12 via the second extending portion 82 by screwing.

It is not necessary to form a groove portion corresponding to the guide groove 81*a* of the first extending portion 81 in the second extending portion 82. Therefore, in the embodiment, the second extending portion 82 is formed in a square columnar shape. That is, the second extending portion 82 has a portion which overlaps the first extending portion 81 when seen in the Z direction, and also has a portion which overlaps a space having a square columnar shape formed by the guide groove 81*a* when seen in the Z direction. However, for example, in order to commonize the members, the second extending portion 82 may be formed into an L-shaped columnar member having the same dimension as that of the first extending portion 81 and may be disposed to completely overlap the first extending portion 81 when seen in the Z direction.

As described above, in the embodiment, the first extending portion 81 and the second extending portion 82 are provided on the protruding portions 22 provided at the corner portions (the four corners) of the main body 21. That is, the first extending portion 81 and the second extending portion 82 are provided at positions corresponding to the corner portions 31*d* of the radiation detection panel 30 (the substrate 31). Additionally, the side wall 13 is formed in a rectangular ring shape when seen in the Z direction, and a recess 13*c* is formed at a corner portion of the side wall 13 to avoid interference with the protruding portion 22, the first extending portion 81, and the second extending portion 82. A thickness t1 of the side wall 13 in the recess 13*c* is smaller than a thickness t2 of the side wall 13 in a side portion which connects the adjacent corner portions. In the embodiment, the recess 13*c* is formed at the corner portion of the side wall 13 to be spaced apart from an outer edge of the protruding portion 22 when seen in the Z direction by cutting out a part of an inner side surface of the side wall 13. Stress concentration on the corner portion of the side wall 13 is curbed by forming the recess 13*c* having such a small thickness at the corner portion of the side wall 13.

Here, the above-described screw hole 13*b* is not provided in the recess 13*c* having a small thickness (a portion having the thickness t1), but is provided only in a side portion having a large thickness (a portion having the thickness t2). Therefore, the top wall 11 and the side wall 13 are not fixed (not screwed) to each other at the corner portions (the four corners) of the housing 10 when seen in the Z direction. However, instead, in the embodiment, as described above, the top wall 11 and the first extending portion 81 may be fixed to each other by the screw member 14. That is, the top wall 11 and the side wall 13 are firmly fixed to each other even at the corner portions of the housing 10. Thus, excellent surface contact between the shield member 112 of the top wall 11 and the side wall 13 can be achieved even at the corner portions of the housing 10 (the portions to which the top wall 11 and the side wall 13 are not directly screwed). As a result, leakage of electromagnetic waves from outside the housing 10 (invasion thereof into the housing 10) can be effectively curbed.

Further, an exterior of the housing 10 seen in the Z direction can be made as small as possible by forming such a recess 13*c*. That is, in order to screw the top wall 11 and the side wall 13 at the corner portions of the housing 10, it is also necessary to increase the exterior size of the housing 10 when seen in the Z direction to secure a thickness of the side wall 13 required for providing the screw holes 13*b* at the corner portions of the housing 10. In this case, a proportion of a dead region in the radiation imaging device 1 when seen in the Z direction (that is, a ratio of a region other than an effective light receiving area (the detection region R) to the entire region of the radiation imaging device 1) becomes large. On the other hand, it is possible to reduce the proportion of the dead region while excellent surface contact between the top wall 11 and the side wall 13 is ensured by forming the recess 13*c* and fixing the first extending portion 81 and the top wall 11 to each other instead of fixing the top wall 11 and the side wall 13 at the corner portions of the housing 10 as described in the embodiment.

Next, an operation (radiation detection) of the radiation imaging device 1 will be described. In the embodiment, a vertical shift register (a vertical scanning circuit) is formed on the IC chip 42 of the flexible circuit substrate 40 connected to the electrode pad 33 formed on the peripheral edge of the substrate 31 in the X direction. Specifically, the vertical shift register 42*a* is formed by the IC chip 42 of the flexible circuit substrate 40 provided on a left peripheral edge portion (a left side) of the substrate 31 in FIG. 1, and the vertical shift register 42*b* is formed by the IC chip 42 of the flexible circuit substrate 40 provided on a right peripheral edge portion (a right side) of the substrate 31. Further, an amplifier chip (a signal connection part) for reading a signal is formed on the IC chip 42 of the flexible circuit substrate 40 connected to the electrode pad 33 formed on the peripheral edge of the substrate 31 in the Y direction. Specifically, the signal connection part 42*c* is formed by the IC chip 42 of the flexible circuit substrate 40 provided on an upper peripheral edge portion (an upper side) of the substrate 31 in FIG. 1, and the signal connection part 42*d* is formed by the IC chip 42 of the flexible circuit substrate 40 provided on a lower peripheral edge portion (lower side) of the substrate 31. As described above, in the embodiment, a configuration in which a signal reading line (a data line) is divided into upper and lower parts is adopted to reduce noise in signal reading and to improve a speed thereof.

Figure 3:
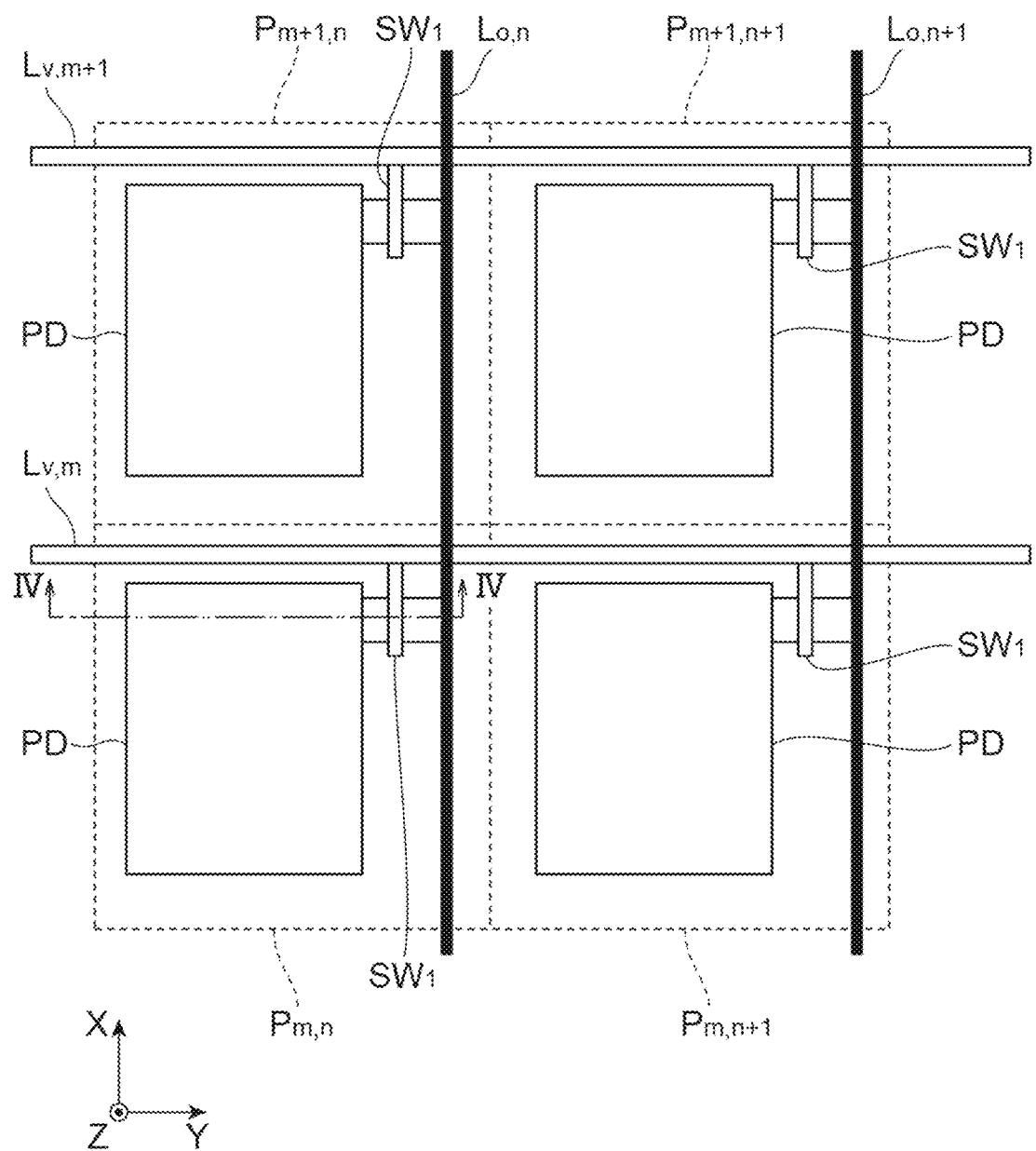
FIG. 3 is an enlarged plan view of a part of a radiation detection panel.
Figure 4:
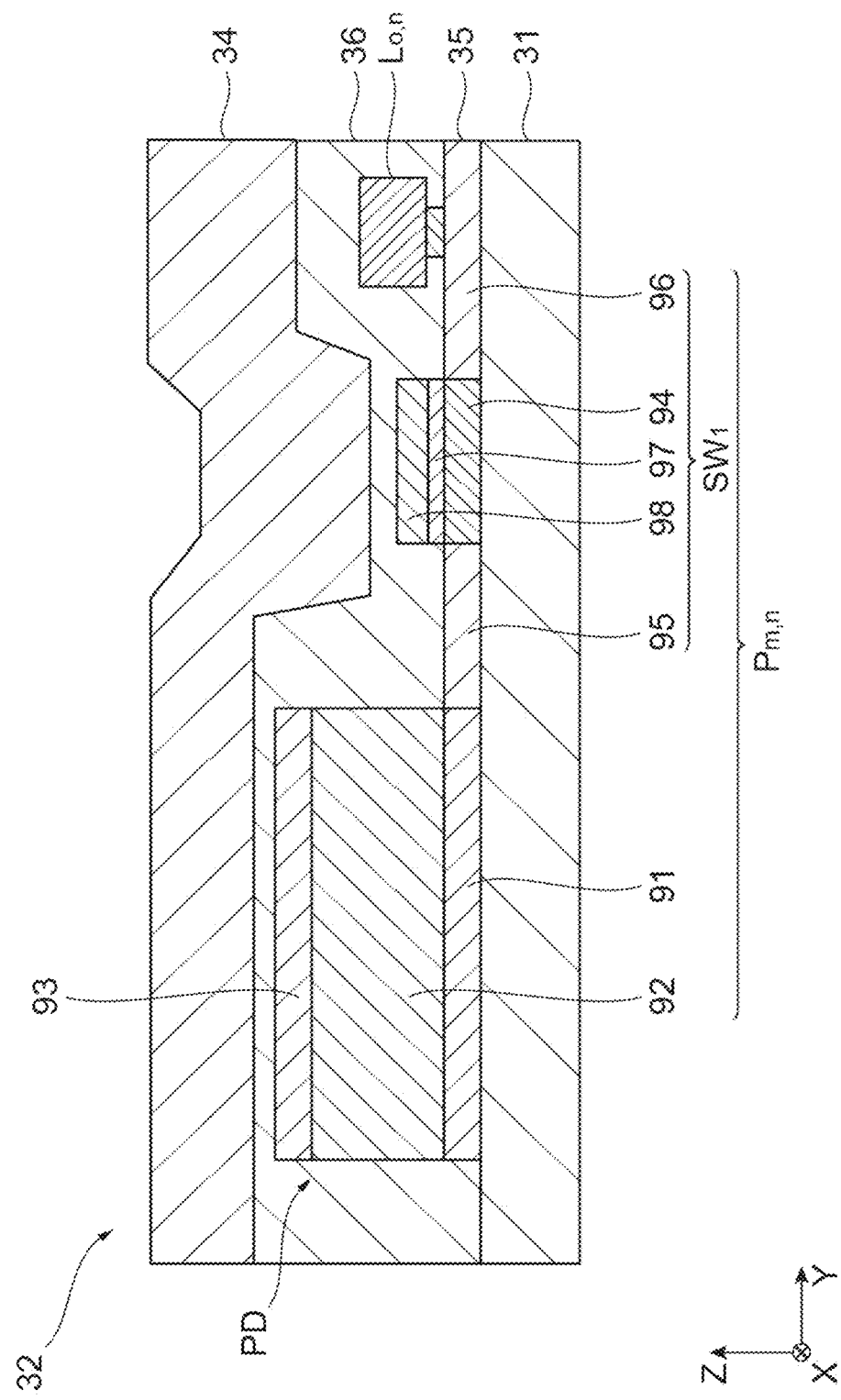
FIG. 4 is a cross-sectional view taken along line IV-IV of FIG. 3.
Figure 5:
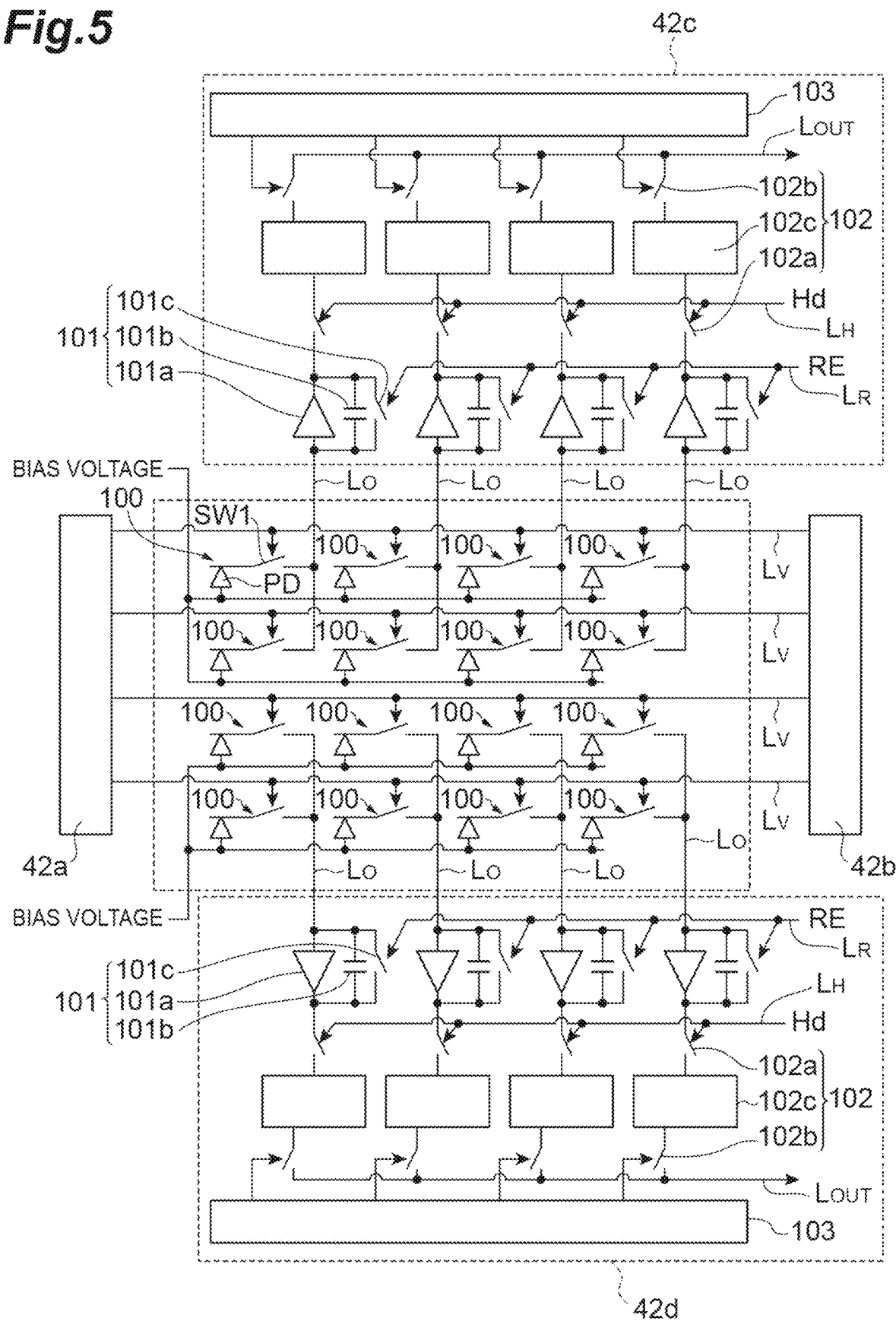
FIG. 5 is a diagram showing an internal configuration of a light receiving part and an IC chip.

A detailed configuration of the light receiving part 32 and the IC chip 42 (the operation of the radiation imaging device 1) will be described with reference to FIGS. 3 to 5. FIG. 3 is an enlarged plan view of a part of the radiation detection panel 30. FIG. 4 is a cross-sectional view taken along line IV-IV of FIG. 3. FIG. 5 is a diagram showing an internal configuration of the light receiving part 32 and the IC chip 42.

The light receiving part 32 is configured by arranging M×N pixels in M rows and N columns in two dimensions. A pixel $P_{m,n}$ shown in FIG. 3 is a pixel located in the mth row and the nth column. Here, in is an integer of 1 or more and M or less, and n is an integer of 1 or more and N or less. In FIG. 3, a column direction coincides with an X-axis direction, and a row direction coincides with a Y-axis direction. Each of a plurality of pixels $P_{1,1}$ to $P_{M,N}$ included in the light receiving part 32 includes a photodiode PD and a reading switch SW1. A bias voltage is applied to an anode terminal of the photodiode PD, and one end (one current terminal) of the reading switch SW1 is connected to a cathode terminal of the photodiode PD. Further, the other end (the other current terminal) of the reading switch SW1 is connected to a corresponding reading wire (for example, in the case of the pixel $P_{m,n}$, an nth column reading wire $L_{o,n}$). A control terminal of the reading switch SW1 is connected to a corresponding row selection wire (for example, in the case of the pixel $P_{m,n}$, an mth row selection wire $L_{v,m}$).

As shown in FIG. 4, a silicon film 35 is provided on the entire surface of the first surface 31a of the substrate 31. Additionally, the photodiode PD, the reading switch SW1, and the nth column reading wire $L_{o,n}$ are formed on a surface of the silicon film 35. The photodiode PD, the reading switch SW1, and the nth column reading wire $L_{o,n}$ are covered with an insulating layer 36. A scintillator 34 is provided on the insulating layer 36 to cover the entire detection region R of the first surface 31a of the substrate 31. The photodiode PD is configured to contain, for example, amorphous silicon.

The photodiode PD of the embodiment includes an n-type semiconductor layer 91 made of n-type polycrystalline silicon, an i-type semiconductor layer 92 made of i-type amorphous silicon provided on the n-type semiconductor layer 91, and a p-type semiconductor layer 93 made of p-type amorphous silicon provided on the i-type semiconductor layer 92. Further, the reading switch SW1 is a thin film transistor (TFT) made of polycrystalline silicon, and has a configuration as a field effect transistor (FET). That is, the reading switch SW1 includes a channel region 94, a source region 95 disposed along one side surface of the channel region 94, a drain region 96 disposed along the other side surface of the channel region 94, and a gate insulating film 97 and a gate electrode 98 formed on the channel region 94. The nth column reading wire $L_{o,n}$ is made of a metal. The scintillator 34 generates scintillation light according to incident radiation, converts a radiation image into an optical image, and outputs the optical image to the light receiving part 32.

In FIG. 5, 4×4 pixels 100 are shown on behalf of M×N pixels $P_{m,n}$ (m=1, . . . , M, n=1, . . . , N). Each of the pixels 100 includes the photodiode PD and the reading switch SW1. The photodiode PD generates an electric charge in an amount corresponding to an intensity of incident light, and accumulates the generated electric charge in a junction capacitance part. As described above, the reading switch SW1 is connected to the row selection wire $L_V$ corresponding to the row to which the pixel 100 belongs. Here, the row selection wire LV corresponding to the pixel $P_{m,n}$ in the mth row is the above-described mth row selection wire $L_{v,m}$. The M row selection wires $L_v$ are connected to the vertical shift registers 42a and 42b. Each of the vertical shift registers 42a and 42b generates a row selection signal for controlling a conduction state and a non-conduction state of the reading switch SW1 for each row and sequentially provides the row selection signal to the row selection wire $L_V$ in each of the rows.

The reading switch SW1 opens when the row selection signal output from the vertical shift register 42a or 42b to the row selection wire $L_v$ is a non-significant value (for example, a low level). At this time, the electric charge generated by the photodiode PD is accumulated in the junction capacitance part without being output to a corresponding column reading wire $L_o$. Here, the column reading wire $L_o$ corresponding to the pixels $P_{m,n}$ in the nth column is the above-described nth column reading wire $L_{o,n}$. On the other hand, when the row selection signal is a significant value (for example, a high level), the reading switch SW1 closes. At this time, the electric charge generated in the photodiode PD and accumulated in the junction capacitance part is output to the corresponding reading wire $L_o$ via the reading switch SW1. The output charge is sent to an integrating circuit 101 via the reading wire $L_o$. In the embodiment, among the pixels 100 formed in the light receiving part 32, the reading switch SW1 of the pixel 100 located in the row on the side of an upper side of the substrate 31 is connected to the integrating circuit 101 of the signal connection part 42c via the corresponding reading wire $L_o$. On the other hand, among the pixels 100 formed in the light receiving part 32, the reading switch SW1 of the pixel 100 located in the row on the side of a lower side of the substrate 31 is connected to the integrating circuit 101 of the signal connection part 42d via the corresponding reading wire $L_o$. A method of dividing the row on the side of the upper side and the row on the side of the lower side of the substrate 31 is arbitrary. For example, when the number of rows on the side of the upper side of the substrate 31 is N1, and the number of rows on the side of the lower side of the substrate 31 is N2, any of relationships "N1=N2", "N1>N2", and "N1<N2" may be established.

The integrating circuit 101 has a so-called charge integration type configuration including an amplifier 101a, a capacitance element 101b, and a discharge switch 101c. The capacitance element 101b and the discharge switch 101c are connected in parallel with each other and are connected between an input terminal and an output terminal of the amplifier 101a. The input terminal of the amplifier 101a is connected to the column reading wire $L_o$. A reset control signal RE is provided to the discharge switch 101c via a reset wire $L_R$.

The reset control signal RE instructs an opening and closing operation of the discharge switch 101c of each of N integrating circuits 101. For example, when the reset control signal RE is a non-significant value (for example, a high level), the discharge switch 101c is closed, the electric charge in the capacitance element 101b is discharged, and an output voltage value of the integrating circuit 101 is initialized. Further, when the reset control signal RE is a significant value (for example, a low level), the discharge switch 101c is opened, the electric charge input to the integrating circuit 101 is accumulated in the capacitance element 101b, and a voltage value corresponding to the accumulated electric charge is output from the integrating circuit 101.

Each of the signal connection parts 42c and 42d further includes N holding circuits 102 and a horizontal shift register 103. Each of the holding circuits 102 includes an input switch 102a, an output switch 102b, and a voltage holding part 102c. One end of the voltage holding part 102c is connected to an output end of the integrating circuit 101 via the input switch 102a, and the other end of the voltage holding part 102c is connected to a voltage output wire $L_{OUT}$ via the output switch 102b. A holding control signal Hd is provided to the input switch 102a via a holding wire $L_H$. The holding control signal Hd instructs an opening and closing operation of the input switches 102a of each of the N holding circuits 102. A column selection signal is provided to the output switch 102b of the holding circuit 102 from the horizontal shift register 103. The column selection signal instructs an opening and closing operation of the output switch 102b of the holding circuit 102 in the corresponding column.

When the holding control signal Hd changes from a high level to a low level, the input switch 102a changes from a closed state to an open state, and the voltage value input to the holding circuit 102 at that time is held by the voltage holding part 102c. After that, when the column selection signal from the horizontal shift register 103 sequentially changes from the low level to the high level for each of the columns, the output switch 102b is sequentially closed, and the voltage value held in the voltage holding part 102c is sequentially output to the voltage output wire $L_{OUT}$ for each of the columns.

Figure 6:
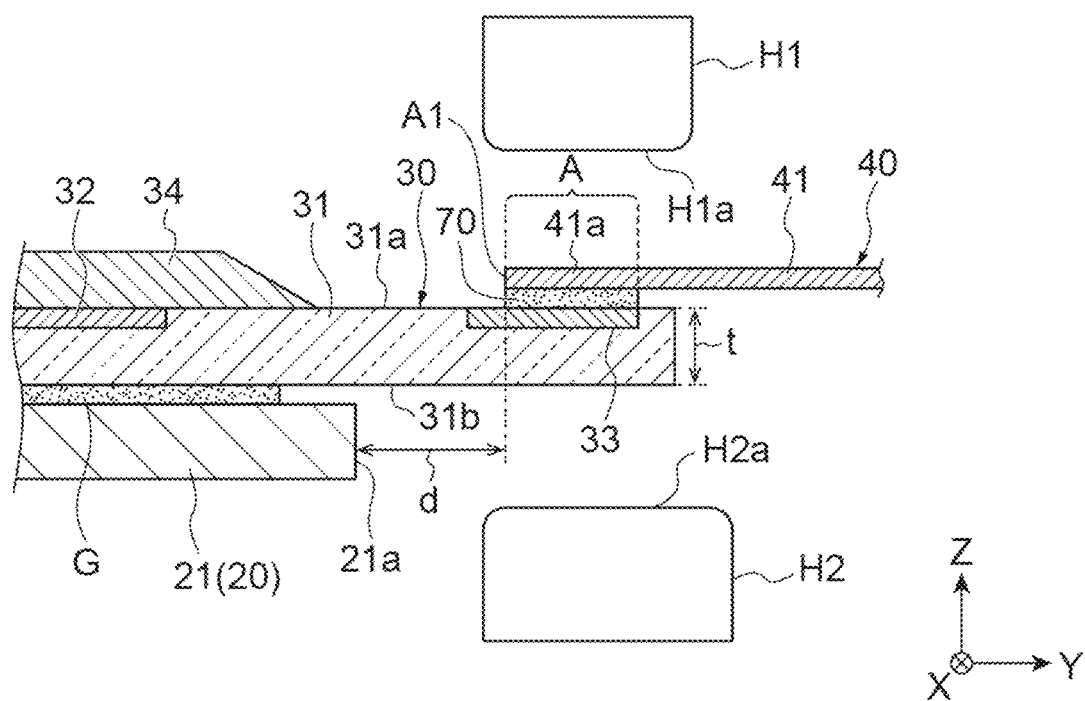
FIG. 6 is a diagram for explaining a positional relationship between a connection region and a base substrate.

Next, with reference to FIG. 6, a positional relationship between the connection region A and the end portion 21a of the base substrate 20 (the main body 21) will be described. As shown in FIG. 6, the one end portion 41a of the flexible circuit substrate 40 is connected to the electrode pad 33 via the connecting member 70 by sandwiching the connecting member 70 between heaters H1 and H2 from above and below and heating (thermocompression bonding) it in a state in which the connecting member 70 is sandwiched between the one end portion 41a and the electrode pad 33. The heater H1 (a first heater) is a crimping jig disposed on the side opposite to the connecting member 70 with the flexible circuit substrate 40 interposed therebetween. The heater H1 is a cemented carbide made of, for example, tungsten carbide and cobalt. The heater H2 (a second heater) is a crimping jig disposed on the side opposite to the connecting member 70 with the heater H1 and the radiation detection panel 30 (that is, the substrate 31) interposed therebetween. The heater H2 is, for example, quartz glass.

When the flexible circuit substrate 40 is connected to the electrode pad 33, a surface H1a (a surface which faces the one end portion 41a) of the heater H1 is brought into contact with the one end portion 41a of the flexible substrate 41 to overlap at least the connection region A when seen in the Z direction. Further, a surface H2a (a surface of the substrate 31 which faces the second surface 31b) of the heater H2 is brought into contact with the second surface 31b of the substrate 31 to overlap at least the connection region A when seen in the Z direction. In this state, for example, heating is performed for several seconds by the heater H1 heated to 190° C. and the heater H2 fixed at 40° C. In order to perform such thermocompression bonding (particularly, contact of the heater H1 with the second surface 31b of the substrate 31), a distance d from the inner end portion A1 of the connection region A to the end portion of the base substrate 20 (the end portion 21a of the main body 21) is preferably 10 μm or more to curb interference between the heater H2 and the base substrate 20 during a work.

On the other hand, any of the heat generated from the heaters H1 and H2 during the thermocompression bonding can be transferred to the light receiving part 32, the scintillator 34, and the adhesive member G via the substrate 31. The heat transferred in this way may adversely affect these members. Here, as described above, the light receiving part 32, the scintillator 34, and the adhesive member G are all located further inward than the end portion 21a of the base substrate 20 when seen in the Z direction. That is, a distance (a distance along the XY plane) from the inner end portion A1 of the connection region A to each of the light receiving part 32, the scintillator 34, and the adhesive member G is guaranteed to be longer than the distance d. Therefore, it is possible to secure a distance (a separation distance longer than the distance d) from the connection region A to each of the members (the light receiving part 32, the scintillator 34, and the adhesive member G) by adjusting the distance d. From the viewpoint of curbing the adverse effect of the heat generated from the heaters H1 and H2 on each of the members as described above, the distance d is preferably 1 mm or more.

Further, when a material having a deliquescent property is used as the scintillator 34, a moisture-proof film (a protective film) formed by parylene or the like may be provided to cover the entire scintillator 34. It is known that a moisture-proof property of such a moisture-proof film decreases at about 50° C. In such a case, the distance d may be set so that a temperature of the scintillator 34 (the moisture-proof film) can be curbed to a temperature required for maintaining the moisture-proof property (here, 50° C. or less).

FIG. 7 shows a simulation result when the thermocompression bonding is performed for 8 seconds with the heater H1 at 200° C. and the heater H2 at 40° C. (A) of FIG. 7 shows a relationship between a distance from the heater H1 (a distance along the Y axis in FIG. 6) and a temperature of the substrate 31 at a portion corresponding to the distance when the substrate 31 is a glass substrate (here, non-alkali glass having a thermal conductivity of 1.2 W/mK). (B) of FIG. 7 shows a relationship between the distance from the heater H1 and the temperature of the substrate 31 at the portion corresponding to the distance when the substrate 31 is a flexible substrate (here, a film material having a thermal conductivity of 0.3 W/mK). When the substrate 31 is a glass substrate, the simulations have been performed for each of cases in which the thickness t of the substrate 31 is 0.3 mm, 0.5 mm, 0.7 mm, and 0.9 mm. On the other hand, when the substrate 31 is a flexible substrate, the simulations have been performed for each of cases in which the thickness t of the substrate 31 is 0.1 mm and 0.2 mm.

As shown in (A) of FIG. 7, in the case in which the substrate 31 is the above-described glass substrate, it is confirmed that when the distance from the heater H1 is about 3.5 mm or more, it can be curbed to 50° C. or less in any one of the thicknesses (0.3 mm, 0.5 mm, 0.7 mm, 0.9 mm) Also, as shown in (B) of FIG. 7, in the case in which the substrate 31 is the above-described flexible substrate, it is confirmed that when the distance from the heater H1 is about 1.5 mm or more, it can be curbed to 50° C. or less in any one of the thicknesses (0.1 mm, 0.2 mm) Here, a distance (a length in the Y direction) from a reference position of the distance from the heater H1 to the inner end portion A1 of the connection region A is 0.27 mm. Further, as described above, an edge portion of the scintillator 34 is located further inward than the end portion 21a of the base substrate 20 when seen in the Z direction. Therefore, from the viewpoint of curbing the temperature of the scintillator 34 (the moisture-proof film) to 50° C. or less, when the substrate 31 is the above-described glass substrate, the distance d is preferably 3.23 mm or more, and when the substrate 31 is the above-described flexible substrate, the distance d is preferably 1.23 mm or more.

Next, an example of a method for manufacturing the radiation imaging device 1 will be described with reference to FIGS. 8 to 11.

First, as shown in (A) of FIG. 8, the radiation detection panel 30 on which the scintillator 34 is formed is prepared. For example, the quality of the radiation detection panel 30 is determined by performing an image inspection such as probing on the radiation detection panel 30. Subsequently, the scintillator 34 is formed by depositing a scintillator material such as CsI on a pixel area (the light receiving part 32) of the radiation detection panel 30 determined as a non-defective product. Thus, the radiation detection panel 30 shown in (A) of FIG. 8 is prepared.

Further, as shown in (B) of FIG. 8, the base substrate 20 on which the first extending portion 81 and the second extending portion 82 are mounted is prepared. For example, the base substrate 20 including the above-described main body 21 and protruding portion 22 is produced by performing planar shape processing on a single metal plate. Subsequently, the first extending portion 81 is mounted on the support surface 20a of the protruding portion 22 (each of the four protruding portions 22 provided at the four corners of the main body 21 in the embodiment) by screwing or the like. Further, the second extending portion 82 is mounted on the back surface 20b of the protruding portion 22 by screwing or the like. Further, the support member 55 for fixing the control substrate 50 is mounted on the back surface 20b of the main body 21. When the first extending portion 81 and the second extending portion 82 are individually screwed using different screws, the second extending portion 82 may not be necessarily mounted on the protruding portion 22 at this stage. In this case, the second extending portion 82 may be mounted on the protruding portion 22 at an arbitrary time point prior to a step of accommodating the second extending portion 82 in a box portion of the housing which will be described later (refer to FIG. 11). Further, the support member 55 may not be necessarily mounted on the main body 21 at this stage and may also be mounted on the main body 21 at an arbitrary time point prior to a mounting step of the control substrate 50 (refer to (A) of FIG. 9) which will be described later.

Subsequently, as shown in (C) of FIG. 8, the radiation detection panel 30 (refer to (A) of FIG. 8) on which the scintillator 34 is formed is fixed to the support surface 20a of the base substrate 20 (refer to (B) of FIG. 8) on which the first extending portion 81 and the second extending portion 82 are mounted. Here, the radiation detection panel 30 (the substrate 31) is positioned using the guide grooves 81a of the first extending portion 81 provided at the four corners (the protruding portions 22) of the base substrate 20 when seen in the Z direction. Subsequently, for example, the substrate 31 is fixed to the support surface 20a of the base substrate 20 by an adhesive member G (refer to FIG. 6) such as a double-sided tape provided in advance on the second surface 31b of the substrate 31. Here, the base substrate 20 is disposed with respect to the radiation detection panel 30 not to overlap the connection region A (refer to FIGS. 2 and 6) in which the electrode pad 33, the connecting member 70, and the flexible circuit substrate 40 will overlap each other. In the embodiment, as a result of positioning the substrate 31 by the guide groove 81a of the first extending portion 81, the end portion 21a of the main body 21 of the base substrate 20 is disposed further inward than the end portion 31c of the substrate 31. Thus, the base substrate 20 is disposed not to overlap the connection region A. In a state shown in (C) of FIG. 8, the radiation detection panel 30 and the base substrate 20 can be easily carried by gripping the portion (in the embodiment, at least one of the protruding portion 22, the first extending portion 81, and the second extending portion 82) at which the protruding portion 22 is provided. That is, handleability of the radiation detection panel 30 and the base substrate 20 is improved by the portion in which the protruding portion 22 is provided.

Subsequently, as shown in (A) of FIG. 9, the control substrate 50 is fixed to the back surface 20b of the base substrate 20 via the support member 55.

Subsequently, as shown in (B) of FIG. 9, the one end portion 41a of the flexible circuit substrate 40 is connected to the electrode pad 33 via the connecting member 70. For example, each of the IC chips 42 is inspected in advance, and the IC chip 42 determined as a non-defective product in the inspection is mounted on the flexible substrate 41. Subsequently, in the state in which the IC chip 42 is mounted on the flexible substrate 41, other inspections (for example, confirmation of conduction between the IC chip 42 and the flexible substrate 41) are further performed. Through such inspections, the flexible circuit substrate 40 which will be mounted on the electrode pads 33 of the substrate 31 (36 electrode pads 33 in the embodiment) is prepared. A mounting order of the control substrate 50 and the flexible circuit substrate 40 may be reversed from the above. That is, the control substrate 50 may be mounted on the base substrate 20 after the flexible circuit substrate 40 is mounted on the radiation detection panel 30.

Subsequently, the connecting member 70 is heated (thermocompression bonded) by the heater H1 disposed on the side opposite to the connecting member 70 with the flexible circuit substrate 40 (the one end portion 41a) interposed therebetween and the heater H2 disposed on the side opposite to the connecting member 70 with the radiation detection panel 30 (the substrate 31) interposed therebetween. As described above, interference between the heater H2 and the base substrate 20 is prevented by disposing the base substrate 20 not to overlap the connection region A. Further, in the embodiment, since the substrate 31 is a transparent glass substrate, a position of the electrode pad 33 can be confirmed from the back surface (the second surface 31b) side of the substrate 31. Thus, positioning of the heater H2 can be easily performed. Each of the electrode pads 33 and each of the flexible circuit substrates 40 are electrically connected by the above-described processing. Although it is difficult to grip each of the side portions of the substrate 31 after the flexible circuit substrate 40 is mounted on the electrode pads 33 disposed on each of the side portions of the substrate 31, the radiation detection panel 30 and the base substrate 20 can be easily carried by gripping the portion at which the protruding portion 22 is provided as described above.

Subsequently, as shown in (A) of FIG. 10, a radiation shielding member 60 for shielding radiation directed to the IC chip 42 mounted on each of the flexible circuit substrates 40 is provided at an edge portion of the back surface 20b of the base substrate 20.

Subsequently, as shown in (B) of FIG. 10, the other end portion 41b of each of the flexible circuit substrates 40 is connected to the control substrate 50 (the connector 51). Thus, each of the flexible circuit substrates 40 and the control substrates 50 are electrically connected. As a result, as shown in (B) of FIG. 10, a detection unit 1a before it is mounted in the housing 10 is completed.

Subsequently, an operation check is performed in the state shown in (B) of FIG. 10. Here, when a defect in the flexible circuit substrate 40 (for example, a malfunction of the IC chip 42 mounted on the flexible circuit substrate 40) is found, a repair work (a repair method of one embodiment) is carried out according to the following procedure.

First, the other end portion 41b of the flexible circuit substrate 40 (hereinafter, "first flexible circuit substrate") in which a defect is found is removed from the connector 51, and the radiation shielding member 60 provided corresponding to the first flexible circuit substrate is removed from the back surface 20b of the base substrate 20. Here, since the radiation shielding member 60 is partially provided for one or each of the plurality of IC chips 42, it is only necessary to remove a part of the radiation shielding member 60, and workability is improved.

Subsequently, the first flexible circuit substrate (the one end portion 41a) is removed from the electrode pad 33 in a state in which the radiation detection panel 30 is supported by the base substrate 20. Specifically, the connecting member 70 is removed from the electrode pad 33 by heating the connecting member 70. The first flexible circuit substrate (the one end portion 41a) can be removed from the electrode pad 33 by removing the connecting member 70 from the electrode pad 33 in this way. As a result, a state shown in (A) of FIG. 9 is obtained. The heating of the connecting member 70 when the first flexible circuit substrate is removed may be performed by the heaters H1 and H2 as in the case of mounting, or may be performed by another method. For example, the connecting member 70 may be heated by blowing hot air onto one side of the connecting member 70 (for example, the side of the first flexible circuit substrate (the one end portion 41a)) using an air gun or the like, instead of using the heaters H1 and H2.

Subsequently, the flexible circuit substrate 40 (a second flexible circuit substrate) which will be mounted on the radiation detection panel 30 is prepared. For example, when the above-described first flexible circuit substrate can be repaired (for example, when the IC chip 42 mounted on the first flexible circuit substrate can be repaired by replacing it with another IC chip), a repair work of the first flexible circuit substrate may be performed. In this case, the repaired first flexible circuit substrate is used as the second flexible circuit substrate. On the other hand, when the first flexible circuit substrate cannot be repaired, a spare of the flexible circuit substrate prepared in advance may be used as the second flexible circuit substrate.

Subsequently, the second flexible circuit substrate is mounted on the electrode pad 33 in a state in which the radiation detection panel 30 is supported by the base substrate 20. That is, as shown in (B) of FIG. 9, the second flexible circuit substrate is connected to the electrode pad 33 via the connecting member 70 by heating (thermocompression bonding) the connecting member 70 with the heater H1 disposed on the side opposite to the connecting member 70 with the second flexible circuit substrate (the one end portion 41a) interposed therebetween and the heater H2 disposed on the side opposite to the connecting member 70 with the radiation detection panel 30 (the substrate 31) interposed therebetween. The repair of the flexible circuit substrate 40 (that is, the removal of the failed first flexible circuit substrate and the reinstallation of the second flexible circuit substrate (for example, the first flexible circuit substrate after repair or the spare part)) is completed by the above-described procedure. Then, a state shown in (B) of FIG. 10 is obtained by mounting again the radiation shielding member 60 which was once removed for repairing the flexible circuit substrate 40 on the edge portion of the back surface 20b of the base substrate 20 and mounting the other end portion 41b of the second flexible circuit substrate on the connector 51. In this way, the flexible circuit substrate 40 can be repaired without removing the radiation detection panel 30 from the base substrate 20 by the base substrate 20 being disposed not to overlap the connection region A.

Figure 10:
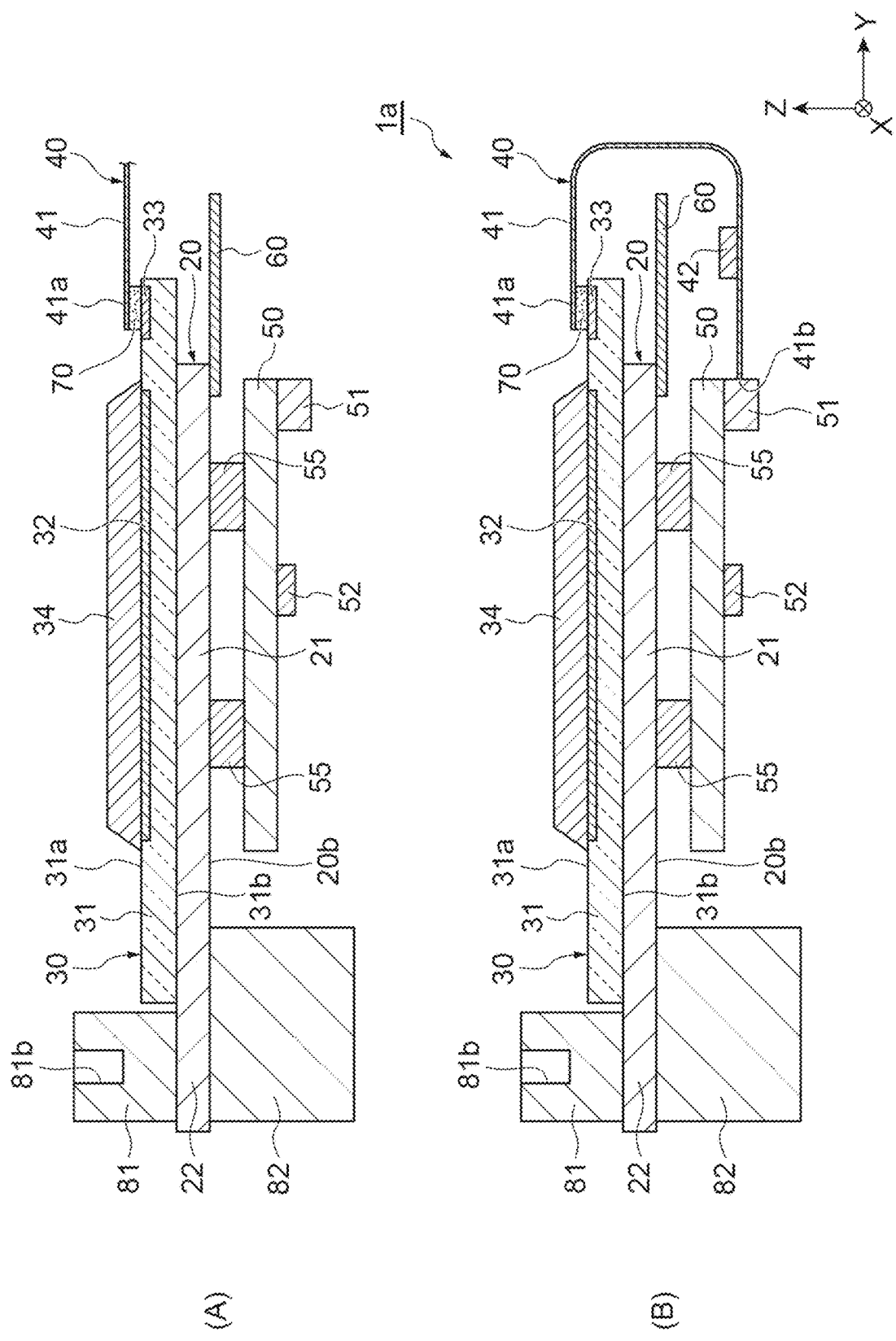
FIG. 10 is a diagram showing the example of the manufacturing process of the radiation imaging device.
Figure 11:
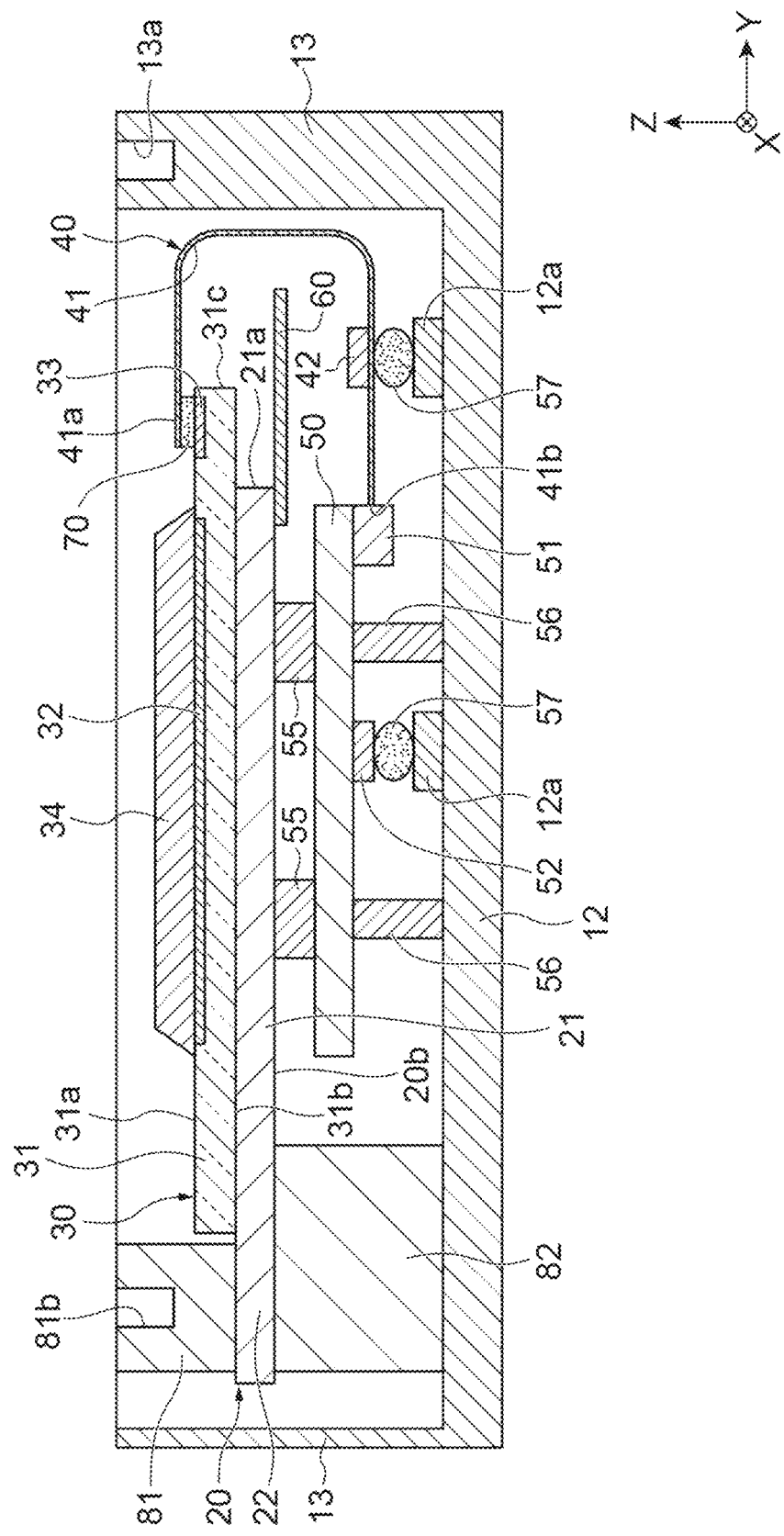
FIG. 11 is a diagram showing the example of the manufacturing process of the radiation imaging device.

Subsequently, as shown in FIG. 11, the detection unit 1a shown in (B) of FIG. 10 is accommodated (fixed) in the box portion (the bottom wall 12 and the side wall 13) of the housing. Specifically, the second extending portion 82 is fixed to the bottom wall 12. Further, the control substrate 50 is fixed to the bottom wall 12 via the support member 56. Further, the heat sink member 57 is disposed between the IC chip 42 or the AD converter 52 and the projection 12a of the bottom wall 12. Subsequently, as shown in FIG. 2, a lid portion (the top wall 11) of the housing is screwed to the side wall 13 and the first extending portion 81. In this way, the radiation imaging device 1 is manufactured. The above-described repair work of the flexible circuit substrate 40 may be performed after the radiation imaging device 1 is completed. In this case, the above-described repair work may be performed after the top wall 11 is removed from the side wall 13 and the first extending portion 81 and the detection unit 1a is removed from the bottom wall 12 to bring the state shown in (B) of FIG. 10.

Next, operational effects of the radiation imaging device 1 will be described.

The radiation imaging device 1 includes the radiation detection panel 30 having the first surface 31a on which the detection region R for detecting radiation is formed and the electrode pad 33 is formed outside the detection region R and the second surface 31b on the side opposite to the first surface 31a, the base substrate 20 having the support surface 20a which faces the second surface 31b of the radiation detection panel 30 and supports the radiation detection panel 30, and the flexible circuit substrate 40 connected to the electrode pad 33 via a connecting member 70. The end portion 21a of the base substrate 20 is located further inward than the inner end portion A1 of the connection region A in which the electrode pad 33, the connecting member 70, and the flexible circuit substrate 40 overlap each other when seen in the Z direction orthogonal to the support surface 20a. In the radiation imaging device 1, when the flexible circuit substrate 40 is connected to the electrode pad 33, it may be necessary to heat the flexible circuit substrate 40, the connecting member 70, and the radiation detection panel 30 with the heaters H1 and H2 from both sides in the Z direction. That is, for example, when a member which generates an adhesive force by thermocompression bonding, such as an anisotropic conductive material, is used as the connecting member 70, thermocompression bonding by the above heaters H1 and H2 is required. On the other hand, in the radiation imaging device 1, the end portion 21a of the base substrate 20 is located further inward than the inner end portion A1 of the connection region A (all the connection regions A in the embodiment) when seen in the Z direction. Therefore, it is possible to avoid interference between the heater H2 disposed on the second surface 31b side of the radiation detection panel 30 and the base substrate 20. Thus, when the repair (repair, replacement, or the like) of the flexible circuit substrate 40 is required, the repair of the flexible circuit substrate 40 can be performed without removing the radiation detection panel 30 from the base substrate 20. Therefore, according to the radiation imaging device 1, the repair work of the flexible circuit substrate 40 can be easily performed.

Further, when the end portion 21a of the base substrate 20 is located further outward than the end portion 31c of the radiation detection panel 30 when seen in the Z direction, it is necessary to route the flexible circuit substrate 40 further outward than the end portion 21a of the base substrate 20. The flexible circuit substrate 40 becomes longer by an amount that such routing is required, and noise easily gets on the signal transmitted through the flexible circuit substrate 40. On the other hand, in the radiation imaging device 1, the end portion 21a of the base substrate 20 is located further inward than the inner end portion A1 of the connection region A when seen in the Z direction (that is, it is located further inward than the end portion 31c of the radiation detection panel 30). Therefore, it is not necessary to route the flexible circuit substrate 40 as described above, and the overall length of the flexible circuit substrate 40 can be shortened. As a result, it is possible to curb noise in the signal transmitted via the flexible circuit substrate 40.

Further, the radiation detection panel 30 is formed in a rectangular shape when seen in the Z direction, and one or more connection regions A are formed on at least one side portion of the radiation detection panel 30. In the embodiment, as an example, a plurality of connection regions A are formed on each of all (four) side portions. The end portion 21a of the base substrate 20 is located further inward than the inner end portions A1 of all the connection regions A formed on at least one side portion (each of the side portions in the embodiment) when seen in the Z direction. With such a configuration, a position of the outer end portion 40a of the flexible circuit substrate 40 connected to the connection region A at the at least one side portion when seen in the Z direction can be brought closer to the end portion 31c of the radiation detection panel 30 without interfering with the end portion 21a of the base substrate 20. That is, the outer end portion 40a of the flexible circuit substrate 40 at the at least one side portion can be located as inward as possible. Thus, the size of the housing 10 when seen in the Z direction can be reduced, and the radiation imaging device 1 can be miniaturized.

Further, the radiation imaging device 1 includes the scintillator 34 which is disposed on the first surface 31a and converts radiation constituting the detection region R into light, the end portion 21a of the base substrate 20 is located further outward than the detection region R when seen in the Z direction, and the distance d (refer to FIG. 6) between the inner end portion A1 of the connection region A and the end portion 21a of the base substrate 20 in a direction along the XY plane (in a second direction) may be 1 mm or more. With such a configuration, it is possible to secure a certain distance (at least 1 mm or more) between the heater H1 which heats the connecting member 70 and the scintillator 34 when the flexible circuit substrate 40 is connected to the electrode pad 33. As a result, the adverse effect of the heat from the heater H1 on the scintillator 34 can be curbed. Further, as described above, a moisture-proof film having a moisture-proof property may be provided at the scintillator 34. Such a moisture-proof film has a property that it is particularly sensitive to heat. With such a configuration, it is possible to curb an adverse effect of the heat from the heater H1 on the scintillator 34 (including the moisture-proof film) having such a particularly heat-sensitive property.

Further, the base substrate 20 has the protruding portion 22 which protrudes further outward than the radiation detection panel 30 (the substrate 31) at a position at which it does not overlap the flexible circuit substrate 40 when seen in the Z direction. With such a configuration, since the protruding portion 22 can be used as a gripping portion in a state in which the radiation detection panel 30 is supported by the base substrate 20, it is possible to improve handleability at the time of manufacturing or repairing the radiation imaging device 1.

Further, the first extending portion 81 which extends in the Z direction is provided on the support surface 20a of the protruding portion 22. The first extending portion 81 serves as a positioning member which positions the radiation detection panel 30 (the substrate 31). With such a configuration, since the first extending portion 81 makes it possible to easily position the radiation detection panel 30 (the substrate 31) with respect to the support surface 20a of the base substrate 20, assembling workability can be improved.

Further, the base substrate 20 is supported on the top wall 11 via the first extending portion 81. With such a configuration, since the base substrate 20 (the protruding portion 22) is supported on the housing 10 (the top wall 11) via the first extending portion 81, the base substrate 20 can be stably supported with respect to the housing 10.

Further, the base substrate 20 is supported on the bottom wall 12 via the second extending portion 82. With such a configuration, the base substrate 20 (the protruding portion 22) is sandwiched by parts of the housing 10 (the top wall 11 and the bottom wall 12) facing each other via the first extending portion 81 and the second extending portion 82. Thus, the base substrate 20 can be stably supported with respect to the housing 10. Here, as a method of supporting the base substrate 20 with respect to the housing 10, as shown in the above-described embodiment, there is, for example, a method of supporting the back surface 20b of the base substrate 20 on the bottom wall 12 via the columnar support members 55 and 56 (or a support member in which the support members 55 and 56 are integrated to support the control substrate 50 while passing through the control substrate 50 in the Z direction). In the embodiment, the above-described support method is used in combination, but since the base substrate 20 is supported by the housing 10 via the first extending portion 81 and the second extending portion 82, it is possible to reduce the number of support members provided on the back surface 20b of the base substrate 20 as compared with a case in which the first extending portion 81 and the second extending portion 82 are not provided. Thus, it is possible to make it difficult for an impact from the outside (particularly the bottom wall 12) to be transmitted to the back surface 20b of the base substrate 20. As a result, it is possible to reduce the impact on the radiation detection panel 30 supported by the base substrate 20. Further, since the number of the support members 56 for supporting the control substrate 50 with respect to the bottom wall 12 can be reduced, it is possible to make it difficult for the impact from the outside (particularly the bottom wall 12) to be transmitted to the control substrate 50. Further, since it is possible to reduce the number of support members passing through the control substrate 50, it is possible to improve a degree of freedom in designing a layout of the control substrate 50 (a layout of circuits, wire, or the like mounted on the control substrate 50).

Further, the first extending portion 81 and the second extending portion 82 may be integrally formed with the base substrate 20, but in the above-described embodiment, the first extending portion 81 and the second extending portion 82 are formed separately from the base substrate 20. With such a configuration, warpage of the base substrate 20 can be reduced as compared with a case in which the base substrate 20 is integrally formed with at least one of the first extending portion 81 and the second extending portion 82. Further, when the first extending portion 81 or the second extending portion 82 is integrally formed with the base substrate 20, it is necessary to cut out a relatively thick metal plate, and thus a disadvantage in which material cost and man-hours are increased occurs. On the other hand, such a disadvantage can be avoided by forming the first extending portion 81 and the second extending portion 82 separately from the base substrate 20.

Figure 9:
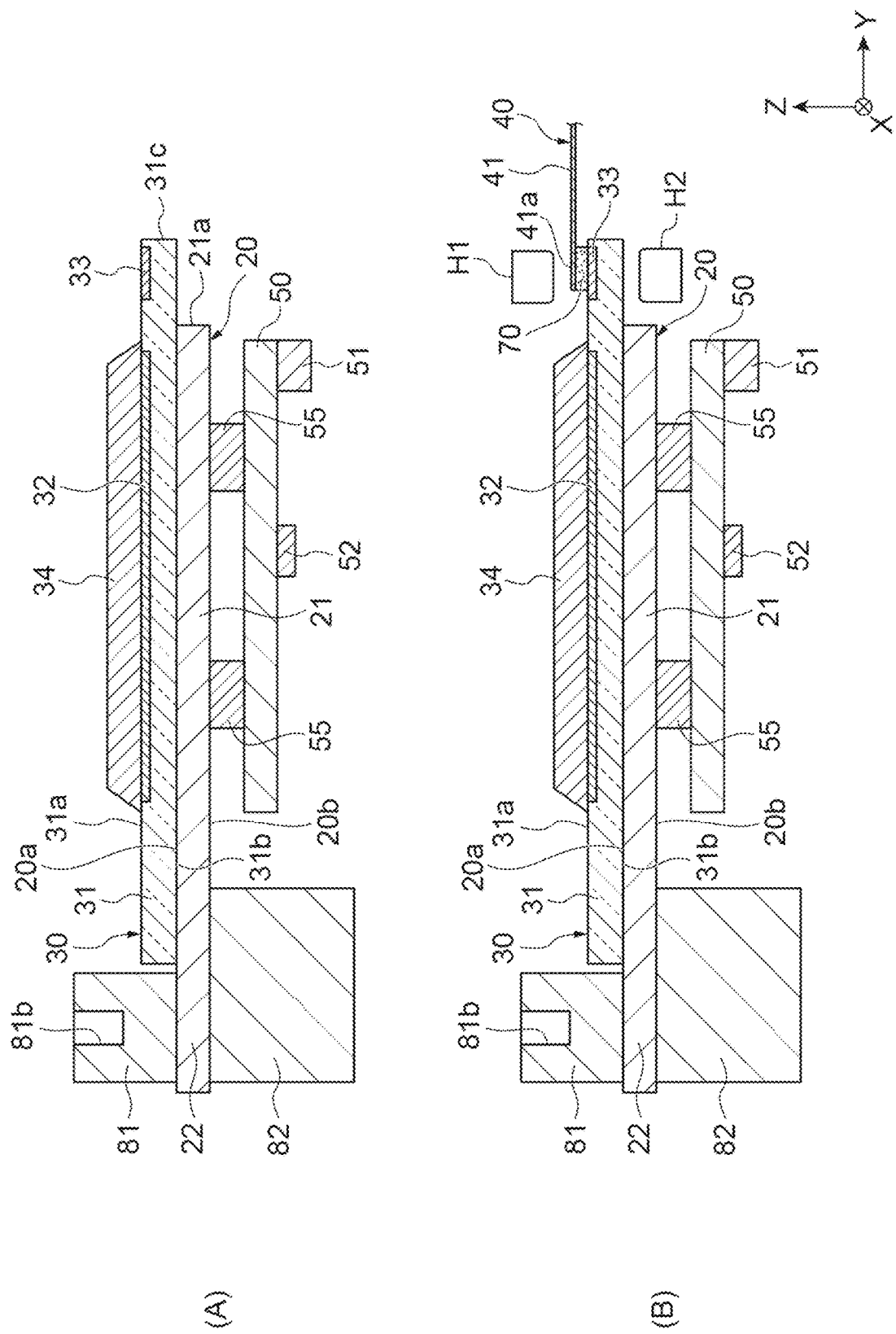
FIG. 9 is a diagram showing the example of the manufacturing process of the radiation imaging device.

Further, the above-described method for manufacturing the radiation imaging device 1 includes a step of preparing the radiation detection panel 30 ((A) of FIG. 8), a step of supporting the second surface 31b of the radiation detection panel 30 on the support surface 20a of the base substrate 20 ((C) of FIG. 8), and a step of connecting the flexible circuit substrate 40 to the electrode pad 33 via the connecting member 70 ((B) of FIG. 9). Additionally, In the supporting step, the base substrate 20 is disposed with respect to the radiation detection panel 30 so that the end portion 21a of the base substrate 20 is located further inward than the inner end portion A1 of the connection region A (refer to FIG. 6) in which the electrode pad 33, the connecting member 70, and the flexible circuit substrate 40 will overlap each other when seen in the Z direction. Also, in the connecting step, the connecting member 70 is heated by the heater H1 disposed on the side opposite to the connecting member 70 with the flexible circuit substrate 40 interposed therebetween and the heater H2 disposed on the side opposite to the connecting member 70 with the radiation detection panel 30 interposed therebetween. According to such a manufacturing method, in the supporting step, the flexible circuit substrate 40, the connecting member 70, and the radiation detection panel 30 can be sandwiched between the heater H1 and the heater H2 and can be thermocompression bonded by disposing the base substrate 20 not to overlap the connection region A. That is, when the flexible circuit substrate 40 and the electrode pad 33 are connected, it is possible to prevent the interference between the heater H2 and the base substrate 20. Thus, the flexible circuit substrate 40 can be connected to the radiation detection panel 30 in a state in which the radiation detection panel 30 is stably supported by the base substrate 20. Further, a sufficient connection strength can be ensured at a lower heating temperature (a heater temperature) by heating from both sides of the connecting member 70 (the flexible circuit substrate 40 side and the radiation detection panel 30 side) with the heaters H1 and H2 as described above, as compared with the case in which the heating is performed from one side of the connecting member 70. Therefore, according to such a manufacturing method, it is also possible to secure the connection strength while the adverse effect of the heat during the heating on the radiation detection panel 30 and the like (for example, the scintillator 34 and the like) is curbed.

However, the manufacturing procedure of the radiation imaging device 1 is not limited to the above-described procedure, and for example, the flexible circuit substrate 40 may be connected to the electrode pad 33 of the radiation detection panel 30 before the radiation detection panel 30 is supported by the base substrate 20. That is, the flexible circuit substrate 40 may be connected to the radiation detection panel 30 in a state in which the radiation detection panel 30 is not supported by the base substrate 20. In any case, since the shape and arrangement of the base substrate 20 are designed not to overlap the connection region A, a degree of freedom of the work procedure at the time of manufacturing the radiation imaging device 1 is improved. Specifically, a timing for carrying out the step of connecting the flexible circuit substrate 40 to the radiation detection panel 30 can be arbitrarily selected. That is, the flexible circuit substrate 40 can be connected to the radiation detection panel 30 before or after the radiation detection panel 30 is supported by the base substrate 20.

Moreover, the above-described repair method of the radiation imaging device 1 includes a step of removing the first flexible circuit substrate from the electrode pad 33 in a state in which the radiation detection panel 30 is supported by the base substrate 20, and a step of connecting the second flexible circuit substrate to the electrode pad 33 via the connecting member 70 by heating the connecting member 70 with the heater H1 disposed on the side opposite to the connecting member 70 with the second flexible circuit substrate (the first flexible circuit substrate after repair or another flexible circuit substrate) interposed therebetween and the heater H2 disposed on the side opposite to the connecting member 70 with the radiation detection panel 30 interposed therebetween in the state in which the radiation detection panel 30 is supported by the base substrate 20. According to such a repair method, the repair (the removing step and the connecting step) of the flexible circuit substrate 40 can be performed without removing the radiation detection panel 30 from the base substrate 20 by disposing the base substrate 20 not to overlap the connection region A. Therefore, according to the above-described repair method, the repair work of the flexible circuit substrate 40 can be easily performed.

(Appendix 1)

The radiation imaging device 1 includes the radiation detection panel 30 having the first surface 31a on which the detection region R for detecting radiation is formed and the second surface 31b on the side opposite to the first surface 31a, the base substrate 20 having the support surface 20a which faces the second surface 31b of the radiation detection panel 30 and supports the radiation detection panel 30, and the flexible circuit substrate 40 connected to the radiation detection panel 30. The end portion 21a of the base substrate 20 corresponding to the portion to which the flexible circuit substrate 40 is connected is located further inward than the end portion 31c of the radiation detection panel 30 when seen in the Z direction orthogonal to the support surface 20a, and the base substrate 20 has the protruding portion 22 which protrudes further outward than the radiation detection panel 30 at a position at which it does not overlap the flexible circuit substrate 40 when seen in the Z direction. In the radiation imaging device 1, the end portion 21a of the base substrate 20 corresponding to the portion to which the flexible circuit substrate 40 is connected is located further inward than the end portion 31c of the radiation detection panel 30 (the substrate 31). Thus, when it is necessary to connect the other end portion 41b of the flexible circuit substrate 40 to the control substrate 50 disposed on the back surface 20b of the base substrate 20 as in the embodiment, interference between the flexible circuit substrate 40 and the base substrate 20 can be appropriately prevented.

Further, from the viewpoint of reducing the proportion of the above-described dead region (that is, the ratio of the region other than the effective light receiving area (the detection region R) to the entire region of the radiation imaging device 1), preferably, a protruding length of the flexible circuit substrate 40 from the end portion 31c of the substrate 31 when seen in the Z direction is as small as possible. Here, the protruding length is a separation distance between the outer end portion 40a (a bent portion which is farthest from the end portion 31c of the substrate 31 in a direction parallel to the XY plane) of the flexible circuit substrate 40 and the end portion 31c of the substrate 31 when seen in the Z direction. Since the end portion 21a of the base substrate 20 is located further inward than the end portion 31c of the radiation detection panel 30 (the substrate 31), the protrusion length can be made as small as possible. Specifically, when the end portion 21a of the base substrate 20 is located further outward than the end portion 31c, there is a restriction that the protruding length should be larger than the distance between the end portion 31c and the end portion 21a of the base substrate 20. On the other hand, since the end portion 21a of the base substrate 20 is located further inward than the end portion 31c of the radiation detection panel 30 (the substrate 31), the above restriction does not occur.

Further, the base substrate 20 has the protruding portion 22 which protrudes further outward than the radiation detection panel 30 (the substrate 31) at a position at which it does not overlap the flexible circuit substrate 40 when seen in the Z direction. Thus, since the protruding portion 22 can be used as a gripping portion in the state in which the radiation detection panel 30 is supported by the base substrate 20, handleability of the base substrate 20 can be improved.

Further, the protruding portions 22 are formed at at least two locations. In this case, the base substrate 20 can be stably gripped at two locations. Further, the protruding portions 22 may be formed at at least three locations or at least four locations. In the embodiment, the protruding portions 22 are formed at four locations. In this case, the base substrate 20 can be gripped more stably.

Further, the substrate 31 (the radiation detection panel 30) is formed in a rectangular shape when seen in the Z direction. The protruding portion 22 is provided at a position corresponding to the corner portion of the radiation detection panel 30. The handleability of the base substrate 20 can be improved by providing the protruding portion 22 at the position corresponding to the corner portion of the substrate 31 while each of the side portions of the substrate 31 is used as a space connected to the flexible circuit substrate 40 (that is, a region in which the electrode pad 33 is formed). In the embodiment, the protruding portions 22 are formed at the four corners of the base substrate 20, and the protruding portions 22 are fixed to the housing 10 via the first extending portion 81 and the second extending portion 82. Thus, the base substrate 20 is supported in a well-balanced manner with respect to the housing 10 via the protruding portions 22 formed at the four corners thereof. Further, in this case, the base substrate 20 is supported on the housing 10 by the protruding portion 22 formed at a position as far as possible from the radiation detection panel 30 when seen in the Z direction. Accordingly, for example, even when the housing 10 is deformed by an external force applied to the housing 10, it is possible to preferably curb spreading of an influence of the deformation of the housing 10 to the radiation detection panel 30 via the base substrate 20.

Further, the radiation detection panel 30 is formed in a rectangular shape when seen in the Z direction, and one or more flexible circuit substrates 40 are connected to at least one side portion of the radiation detection panel 30. In the embodiment, as an example, a plurality of flexible circuit substrates 40 are connected to each of all (four) side portions. The end portion 21a of the base substrate 20 corresponding to the portion to which all the flexible circuit substrates 40 are connected at at least one side portion is located further inward than the end portion 31c of the radiation detection panel 30. With such a configuration, positions of the outer end portions 40a of all the flexible circuit substrates 40 at at least one side portion when seen in the Z direction can be brought closer to the end portion 31c of the radiation detection panel 30 without interfering with the end portion 21a of the base substrate 20. That is, the outer end portion 40a of the flexible circuit substrate 40 at at least one side portion can be located as inward as possible. Thus, the size of the housing 10 when seen in the Z direction can be reduced, and the radiation imaging device 1 can be miniaturized.

(Appendix 2)

According to the radiation imaging device 1, the base substrate 20 (the protruding portion 22) is sandwiched by parts of the housing 10 (the top wall 11 and the bottom wall 12) facing each other via the first extending portion 81 and the second extending portion 82. Thus, the base substrate 20 can be stably supported with respect to the housing 10. Here, as a method of supporting the base substrate 20 with respect to the housing 10, as shown in the above-described embodiment, there is, for example, a method of supporting the back surface 20b of the base substrate 20 on the bottom wall 12 via the columnar support members 55 and 56 (or a support member in which the support members 55 and 56 are integrated to support the control substrate 50 while passing through the control substrate 50 in the Z direction). In the embodiment, the above-described support method is used in combination, but since the base substrate 20 is supported by the housing 10 via the first extending portion 81 and the second extending portion 82, it is possible to reduce the number of support members provided on the back surface 20b of the base substrate 20 as compared with a case in which the first extending portion 81 and the second extending portion 82 are not provided. Thus, it is possible to make it difficult for an impact from the outside (particularly the bottom wall 12) to be transmitted to the back surface 20b of the base substrate 20. As a result, it is possible to reduce the impact on the radiation detection panel 30 supported by the base substrate 20. Further, since the number of the support members 56 for supporting the control substrate 50 with respect to the bottom wall 12 can be reduced, it is possible to make it difficult for the impact from the outside (particularly the bottom wall 12) to be transmitted to the control substrate 50. Further, since it is possible to reduce the number of support members passing through the control substrate 50, it is possible to improve a degree of freedom in designing a layout of the control substrate 50 (a layout of circuits, wire, or the like mounted on the control substrate 50).

Further, as described above, the first extending portion 81 and the second extending portion 82 may be mounted on the protruding portion 22 by a common mounting member (a screw or the like). With such a configuration, a relative positional relationship between the first extending portion 81 and the second extending portion 82 can be maintained with high accuracy, and the base substrate 20 can be supported more stably.

Further, the second extending portion 82 is larger than the first extending portion 81 when seen in the Z direction, and the second extending portion 82 has a portion which does not overlap the first extending portion 81 when seen in the Z direction. In the embodiment, the second extending portion 82 is larger than the first extending portion 81 by an amount that a groove portion corresponding to the guide groove 81a of the first extending portion 81 is not provided. The bottom wall 12 of the housing 10 located on the side opposite to the first surface 31a on which the detection region R of the radiation detection panel 30 is formed (that is, facing the second surface 31b) is usually a ground surface. Therefore, with such a configuration, the base substrate 20 can be supported more stably by making the second extending portion 82 supported by the bottom wall 12 larger than the first extending portion 81. Further, since the impact from the ground contact surface side (the bottom wall 12) can be suitably absorbed by the second extending portion 82, it is possible to make it difficult for the impact to be transmitted to the radiation detection panel 30.

Further, a plurality of first extending portions 81 disposed apart from each other are provided, and a plurality of second extending portions 82 disposed apart from each other to correspond to the plurality of first extending portions 81 are provided on the support surface 20a of the protruding portion 22. In the embodiment, four first extending portions 81 disposed apart from each other and four second extending portions 82 corresponding to the four first extending portions 81 are provided. With such a configuration, the base substrate 20 can be supported with respect to the housing 10 by the first extending portions 81 and the second extending portions 82 scattered at a plurality of positions (in the embodiment, the four corners of the base substrate 20) spaced apart from each other. Thus, for example, as compared with a case in which the first extending portion and the second extending portion are formed in a wall shape along the edge portion of the base substrate 20, the base substrate 20 can be stably supported with respect to the housing 10 while a weight of the first extending portion 81 and the second extending portion 82 is reduced.

Further, the base substrate 20 has a plurality of (four in the embodiment) protruding portions 22 disposed apart from each other, and the first extending portion 81 and the second extending portion 82 are provided on each of the plurality of protruding portions 22. With such a configuration, a configuration in which the above-described effects are achieved can be easily realized by providing the first extending portion 81 and the second extending portion 82 for each of the protruding portions 22. Unlike the above-described embodiment, the plurality of first extending portions 81 which are separated from each other and the plurality of second extending portions 82 which are separated from each other may be provided on one protruding portion 22. Also in this case, the above-described effects can be obtained. However, it is possible to reduce an useless region (a region in which the first extending portion 81 and the second extending portion 82 are not provided) in the protruding portion 22 and it is possible to reduce a size and a weight of the protruding portion 22, by providing one first extending portion 81 and one second extending portion 82 for each of the plurality of protruding portions 22 disposed in a dispersed manner as in the embodiment.

Further, the radiation detection panel 30 is formed in a rectangular shape when seen in the Z direction. The plurality of protruding portions 22 are provided at positions corresponding to the four corners of the radiation detection panel 30. With such a configuration, since the four corners of the base substrate 20 can be sandwiched by the top wall 11 and the bottom wall 12 via the first extending portion 81 and the second extending portion 82 in a well-balanced manner, the base substrate 20 can be supported more stably with respect to the housing 10.

Further, the side wall 13 is formed in a rectangular ring shape when seen in the Z direction. The recess 13c is formed at the corner portion of the side wall 13 to avoid interference with the protruding portion 22, the first extending portion 81, and the second extending portion 82. The thickness t1 of the side wall 13 in the recess 13c is smaller than the thickness t2 of the side wall 13 in the side portion which connects the corner portions of the adjacent side walls 13. When the thickness of the side wall 13 is made constant (that is, the thickness at the corner portion is the same as the thickness at the side portion), it is necessary to increase the exterior size of the housing 10 when seen in the Z direction by an amount that it is necessary to avoid interference with the protruding portion 22 at the corner portion. In this case, the proportion of the dead region in the radiation imaging device 1 when seen in the Z direction becomes large. On the other hand, with such a configuration, it is possible to reduce the proportion of the dead region by forming the recess 13c.

Further, the top wall 11 has a shield member 112 disposed to be in surface contact with the side wall 13, and the top wall 11 is screwed to the side portion of the side wall 13 (the screw hole 13b provided in the side portion of the side wall 13) and the first extending portion 81 (the screw hole 81b provided in the first extending portion 81). With such a configuration, excellent surface contact between the top wall 11 and the side wall 13 can be achieved on the entire upper surface 13a of the side wall 13 by screwing the top wall 11 to the side portion of the side wall 13 and the first extending portion 81 (that is, the portion close to the corner portion of the side wall 13). Thus, an electromagnetic shield effect can be effectively enhanced.

Although the preferred embodiments of the disclosure have been described in detail, the disclosure is not limited to the above-described embodiment. For example, not only the above-described materials and shapes but also various materials and shapes can be adopted as the material and shape of each of the parts.

In the above-described embodiment, the vertical shift registers 42a and 42b and the signal connection parts 42c and 42d are all externally mounted via the flexible circuit substrate 40. Further, in consideration of reading performance (noise, reading speed, and the like), the electrode pads 33 for connecting the vertical shift registers 42a and 42b are disposed on both the left and right sides of the detection region R, and the electrode pads 33 for connecting the signal connection parts 42c and 42d are disposed on both the upper and lower sides of the detection region R. That is, in the above-described embodiment, as shown in (A) of FIG. 12, a plurality of electrode pads 33 are disposed on the four sides surrounding the detection region R. However, the electrode pads 33 may not be necessarily disposed on all the four sides. Further, the number of electrode pads 33 disposed on each of the sides and an arrangement interval thereof are not particularly limited.

For example, one of the vertical shift registers 42a and 42b or one of the signal connection parts 42c and 42d may be omitted. In this case, as shown in (B) of FIG. 12, the electrode pads 33 are disposed along three sides of the substrate 31. Further, one of the vertical shift registers 42a and 42b and one of the signal connection parts 42c and 42d may be omitted. In this case, as shown in (C) of FIG. 12, the electrode pads 33 are disposed along two sides of the substrate 31. Further, for example, the circuit corresponding to the vertical shift registers 42a and 42b may be disposed on the substrate 31 instead of the external IC chip 42. Further, one of the signal connection parts 42c and 42d may be omitted. In this case, as shown in (D) of FIG. 12, the electrode pads 33 are disposed along one side of the substrate 31. For example, arrangement of such a circuit can be easily performed by configuring the substrate 31 as a TFT panel using low-temperature polysilicon.

Figure 12:
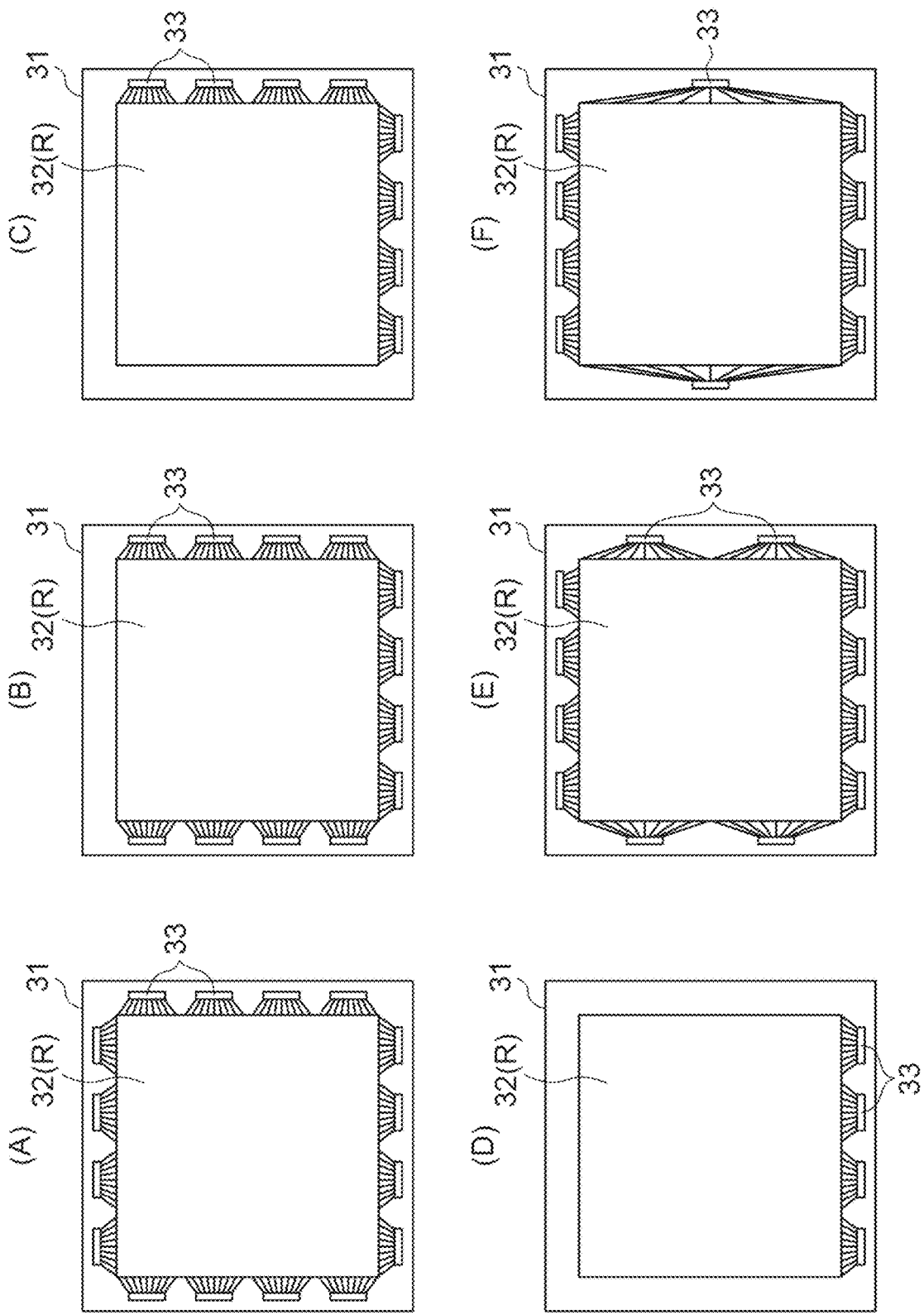
FIG. 12 is a diagram showing an arrangement example of an electrode pad.
Figure 13:
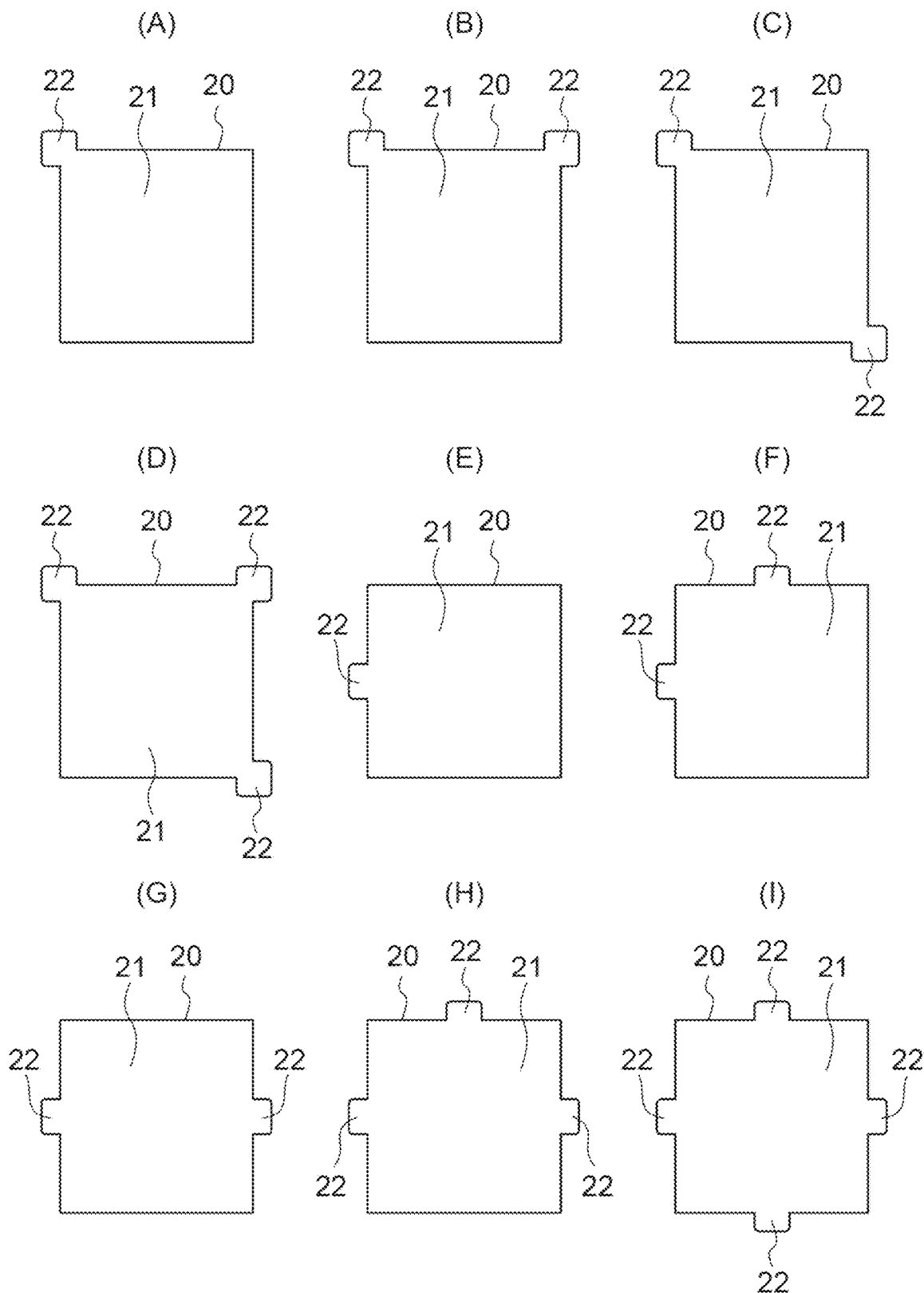
FIG. 13 is a diagram showing a modified example of the base substrate.

Further, as shown in (E) of FIG. 12, a plurality of (here, two as an example) electrode pads 33 may be disposed at relatively wide intervals on the side portions of the substrate 31 (here, two sides on both the left and right sides) at which the electrode pads 33 are provided. In the example, a relatively wide space in which the electrode pads 33 are not disposed is formed at center portions of the two sides on both the left and right sides. Further, as shown in (F) of FIG. 12, only one electrode pad 33 may be disposed on the side portion of the substrate 31 (here, two sides on both the left and right sides) on which the electrode pad 33 is provided, and a relatively wide space may be formed on both sides of the electrode pad 33. Then, as shown in (B) to (F) of FIG. 12, when the side portion in which the electrode pad 33 is not formed or the relatively wide space in which the electrode pad 33 is not provided is provided on the substrate 31, the protruding portion 22 (refer to, for example, (E) to (I) of FIG. 13) may be disposed on the portion corresponding to the side portion or the space.

In the above-described embodiment, the protruding portions 22 are provided at the four corners of the main body 21, but the arrangement and the number of the protruding portions 22 are not limited to the above example. For example, the protruding portions 22 may be provided at one corner portion as shown in (A) of FIG. 13, may be provided at two adjacent corner portions as shown in (B) of FIG. 13, may be provided at two corner portions which are diagonal to each other as shown in (C) of FIG. 13, or may be provided at three corner portions as shown in (D) of FIG. 13.

Further, the position at which the protruding portion 22 is provided is not limited to the corner portion of the main body 21, and may be the side portion of the main body 21. In this case, for example, the protruding portion 22 may be provided on one side as shown in (E) of FIG. 13, may be provided on two sides adjacent to each other as shown in (F) of FIG. 13, may be provided on two sides facing each other as shown in (G) of FIG. 13, may be provided on three sides as shown in (H) of FIG. 13, or may be provided on four sides as shown in (I) of FIG. 13. Further, in the examples of (F) to (I) of FIG. 13, the protruding portion 22 is provided at the center portion of each of the sides, but the protruding portion 22 may be provided at a position deviated from the center portion of each of the sides, or two or more protruding portions 22 may be provided for one side (for example, refer to (D) of FIG. 14). In addition, as shown in (A) to (E) of FIG. 13, even when there is only one protruding portion 22, the radiation detection panel 30 and the base substrate 20 can be easily carried by gripping the protruding portion 22. That is, the handleability of the radiation detection panel 30 and the base substrate 20 is improved by the portion on which the protruding portion 22 is provided. On the other hand, when a plurality of protruding portions 22 are provided, the base substrate 20 can be stably gripped at a plurality of locations, and thus the handleability can be further improved.

Further, the protruding portion 22 may be provided on both the corner portion and the side portion of the main body 21. That is, the arrangement of the protruding portions 22 shown in the above-described embodiment and FIG. 13 and the like may be arbitrarily combined.

In the above-described embodiment, although the first extending portion 81 (the first extending portion 81 in which the guide groove 81a is provided) as the positioning member is provided at a position corresponding to each of the four corners of the substrate 31, at least one first extending portion 81 as the positioning member may be provided. Also in this case, since it is possible to position two sides adjacent to each other (two sides orthogonal to each other) with the corner portion of the substrate 31 interposed therebetween, the substrate 31 can be positioned. However, as shown in (A) to (C) of FIG. 14, the first extending portion 81 as the positioning member is preferably provided at positions corresponding to two or more corner portions of the substrate 31. Thus, workability when the substrate 31 is disposed on the support surface 20a of the base substrate 20 can be improved.

Figure 14:
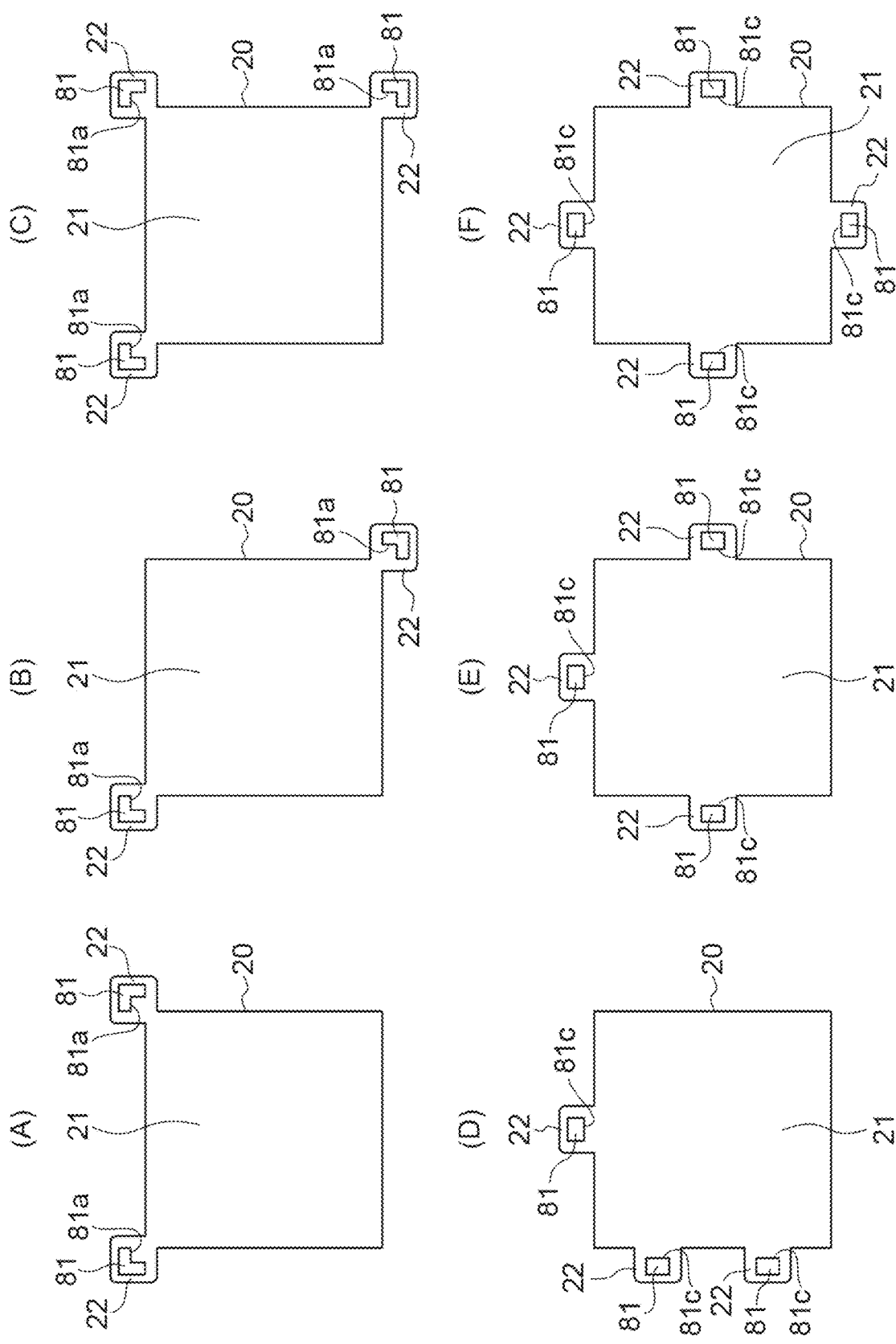
FIG. 14 is a diagram showing an arrangement example of a first extending portion.

Further, as shown in (D) to (F) of FIG. 14, when the protruding portion 22 is provided on the side portion of the main body 21, the first extending portion 81 may have a guide surface 81c (a surface parallel to the side portion of the corresponding substrate 31 when seen in the Z direction) for positioning the side portion of the substrate 31. Further, in this case, at least one (two in total) first extending portion 81 may be provided on each of two sides orthogonal to each other. However, as shown in (D) to (F) of FIG. 14, preferably, the first extending portion 81 as the positioning member is provided at three or more locations. Thus, workability when the substrate 31 is disposed on the support surface 20a of the base substrate 20 can be improved.

Further, the first extending portion 81 as the positioning member may be provided on both the corner portion and the side portion of the main body 21.

The first extending portion 81 used as the positioning member may be removed after the substrate 31 is fixed to the support surface 20a. However, it is possible to prevent occurrence of a handling mistake when the first extending portion 81 is removed, and thus it is possible to prevent damage to members such as the base substrate 20 due to the handling mistake (that is, a decrease in a yield of the radiation imaging device 1) by leaving the first extending portion 81 even after the substrate 31 is fixed to the support surface 20a. Further, the first extending portion 81 can serve as a protective member for protecting the end portion of the substrate 31 (in the above-described embodiment, the corner portion 31d of the substrate 31) by leaving the first extending portion 81. Furthermore, as in the above-described embodiment, the first extending portion 81 can be utilized as a support member for connecting the protruding portion 22 to the top wall 11.

In the above-described embodiment, although the first extending portion 81 serves as the positioning member for positioning the substrate 31 and also serves as the supporting member for supporting the protruding portion 22 with respect to the top wall 11, the first extending portion 81 may have only one function of the positioning member and the supporting member. That is, the portion for positioning the substrate 31 (the guide groove 81a in the embodiment) may not be provided in the first extending portion 81. Alternatively, the first extending portion 81 may not be fixed to the top wall 11. Alternatively, the first extending portion 81 may be omitted. Further, when the plurality of protruding portions 22 are provided, the first extending portion 81 may be provided only on any of the protruding portions 22. Similarly, the second extending portion 82 may be omitted. Further, when the plurality of protruding portions 22 are provided, the second extending portion 82 may be provided only on any of the protruding portions 22.

The protruding portion 22 may be omitted. That is, the base substrate 20 may be a member consisting only of the above-described main body 21. In this case, the first extending portion 81 and the second extending portion 82 fixed to the protruding portion 22 may also be omitted.

In the above-described embodiment, although the base substrate 20 is formed not to overlap all the connection regions A when seen in the Z direction, the base substrate 20 may be formed not to overlap at least one connection region A, and may not necessarily be formed not to overlap all the connection regions A. For example, the base substrate 20 may be formed not to overlap the connection region A corresponding to the flexible circuit substrate 40 on which the IC chip 42 having a particularly high failure rate (that is, repair work is likely to occur) is mounted but to overlap other connection regions A. In this case, although the procedure shown in the above-described embodiment (that is, the procedure of connecting each of the flexible circuit substrates 40 to each of the electrode pads 33 after the radiation detection panel 30 is supported on the base substrate 20) cannot be performed, the radiation imaging device 1 can be manufactured by connecting each of the flexible circuit substrates 40 to the radiation detection panel 30 and then supporting the radiation detection panel 30 on the base substrate 20. Further, when the IC chip 42 breaks down due to the base substrate 20 being formed not to overlap the connection region A corresponding to the flexible circuit substrate 40 on which the IC chip 42 having a high failure rate is mounted, the repair work of the flexible circuit substrate 40 can be performed without removing the radiation detection panel 30 from the base substrate 20. Therefore, even when the base substrate 20 is formed not to overlap only a part of the connection region A in this way, similar to the above-described embodiment, the repair work of the flexible circuit substrate 40 corresponding to the connection region A can be easily performed, and the effect of curbing noise in the signal transmitted via the flexible circuit substrate 40 is achieved.

In the above-described embodiment, although only the flexible circuit substrate 40 is used as an electrical connection means with each of the electrode pad 33, a connection means other than the flexible circuit substrate 40 (for example, wire bonding or the like) may be used in combination. For example, any of the electrode pads 33 may be connected to the control substrate 50 via the flexible circuit substrate 40, and other electrode pads 33 may be connected to the control substrate 50 (or a control circuit provided separately) by wire bonding.

Also, in the above-described embodiment, although the external IC chip 42 and the electrode pad 33 are electrically connected via the flexible circuit substrate 40, for example, a substrate for mounting a chip may be accommodated in the housing 10, and the IC chip may be mounted on the substrate. Further, the IC chip and the electrode pad 33 may be electrically connected only by a connecting means other than the flexible circuit substrate 40 (for example, the above-described wire bonding). Further, in such a case, since the connection region A as described in the above-described embodiment is not present, the end portion 21a of the base substrate 20 may not be disposed further inward than the end portion 31c of the radiation detection panel 30 (the substrate 31) when seen in the Z direction. That is, the base substrate 20 having a size which completely includes the substrate 31 when seen in the Z direction (that is, the base substrate 20 of which the entire peripheral edge portion is located further outward than the substrate 31 when seen in the Z direction) may be used. In this case, the entire peripheral edge portion of the base substrate 20 corresponds to the protruding portion 22 in the above-described embodiment.

Also, in the above-described embodiment, from the viewpoint of preventing interference between the base substrate 20 and the flexible circuit substrate 40 and reducing the proportion of the dead region, the end portion 21a of the base substrate 20 corresponding to the portion to which the flexible circuit substrate 40 is connected may be located further inward than the end portion 31c of the radiation detection panel 30 (the substrate 31), and the base substrate 20 may not be formed not to overlap the connection region A when seen in the Z direction.

In the above-described embodiment, although the detection region R is a region to which an indirect conversion method in which a radiation image is converted into an optical image by the scintillator 34 and then the light image is imaged by the light receiving part 32 to obtain an image is applied, the detection region R may be a region to which a direct conversion method for directly capturing the radiation image to obtain an image is applied. For example, on the first surface 31a of the substrate 31, a pixel circuit configured to accumulate and transfer electric charges may be provided instead of the light receiving part 32, and a solid material (a converting part) (for example, CdTe, CdZnTe, GaAs, InP, TlBr, HgI2, PbI2, Si, Ge, a-Se, or the like) which directly converts radiation into electric charges may be provided instead of the scintillator 34. Thus, the detection region R to which the direct conversion method is applied is obtained. In this case, the detection region R is a region on which radiation is incident and is a region to which a bias voltage is applied (that is, a region for which an image is acquired). Since such a solid material also has a property that it is sensitive to a high temperature like the scintillator 34, preferably, a distance between the solid material and the connection region A (that is, the distance d between the end portion 21a of the base substrate 20 and the inner end portion A1 of the connection region A) is as large as possible. Specifically, even when the solid material is provided (in the direct conversion method), the distance d is preferably set to 1 mm or more, as in the case in which the scintillator 34 is provided (in the indirect conversion method). Thus, a certain distance (at least 1 mm or more) can be secured between the heater H1 which heats the connecting member 70 to connect the flexible circuit substrate 40 to the electrode pad 33 and the solid material. As a result, an adverse effect of the heat from the heater H1 on the solid material can be curbed.

In the above-described embodiment, although the radiation detection panel 30 in which polycrystalline silicon, amorphous silicon, or the like is formed on the substrate 31 which is a glass substrate has been described, the radiation detection panel 30 is not limited to the above-described configuration, and may have a configuration in which the light receiving part is formed on, for example, a single crystal silicon substrate. Further, the substrate 31 is not limited to the glass substrate, and may be, for example, a film-shaped substrate (a flexible substrate) or the like.

REFERENCE SIGNS LIST

1 Radiation imaging device
10 Housing
11 Top wall (first wall portion)
12 Bottom wall (second wall portion)
13 Side wall (third wall portion)
13c Recess
20 Base substrate
20a Support surface
20b Back surface
21a End portion
22 Protruding portion
30 Radiation detection panel
31c End portion
32 Light receiving part
33 Electrode pad
34 Scintillator (conversion part)
40 Flexible circuit substrate
70 Connecting member
81 First extending portion
82 Second extending portion
112 Shield member
A Connection region
A1 Inner end portion
H1 Heater (first heater)
H2 Heater (second heater)

The invention claimed is:

1. A radiation imaging device comprising:
a radiation detection panel having a first surface on which a detection region for detecting radiation is formed and an electrode pad is formed outside the detection region, and a second surface on a side opposite to the first surface;
a base substrate having a support surface configured to face the second surface of the radiation detection panel and configured to support the radiation detection panel;

a flexible circuit substrate comprising:
  a first portion which is connected to the electrode pad via a connecting member and
  a second portion which is bent to at least partially overlap the first portion when seen in a first direction orthogonal to the support surface and on which an IC chip is mounted; and
a radiation shielding member provided at an edge portion of a back surface of the base substrate opposite to the support surface, wherein a part of the radiation shielding member protrudes to the outside of the base substrate so as to extend between the first portion and the second portion of the flexible circuit substrate and to overlap the IC chip when seen in the first direction,
wherein an end portion of the base substrate is located further inward than an inner end portion of a connection region in which the electrode pad, the connecting member, and the flexible circuit substrate overlap each other when seen in the first direction, and
at least a portion of the IC chip is positioned outside of the end portion of the base substrate when seen in the first direction.

2. The radiation imaging device according to claim 1, wherein:
  the radiation detection panel is formed in a rectangular shape when seen in the first direction,
  one or more of the connection regions are formed on at least one side portion of the radiation detection panel, and
  the end portion of the base substrate is located further inward than inner end portions of all the connection regions formed on the at least one side portion when seen in the first direction.

3. The radiation imaging device according to claim 1, further comprising a conversion part disposed on the first surface to constitute the detection region and configured to convert radiation into light or electric charge,
  wherein the end portion of the base substrate is located further outward than the detection region when seen in the first direction, and
  a distance between the inner end portion of the connection region and the end portion of the base substrate in a second direction orthogonal to the first direction is 1 mm or more.

4. The radiation imaging device according to claim 3, wherein the conversion part is a scintillator which converts radiation into light.

5. The radiation imaging device according to claim 1, wherein the base substrate has a protruding portion which protrudes further outward than the radiation detection panel at a position at which the base substrate does not overlap the flexible circuit substrate when seen in the first direction.

6. The radiation imaging device according to claim 5, wherein a first extending portion which extends in the first direction is provided on the support surface of the protruding portion.

7. The radiation imaging device according to claim 6, wherein the first extending portion is a positioning member which positions the radiation detection panel.

8. The radiation imaging device according to claim 6, further comprising a housing configured to accommodate the radiation detection panel, the base substrate, and the flexible circuit substrate,
  wherein the housing has a first wall portion which faces the first surface and a second wall portion which faces the second surface, and
  the base substrate is supported on the first wall portion via the first extending portion.

9. The radiation imaging device according to claim 8, wherein:
  a second extending portion which is disposed at a position at which the second extending portion faces the first extending portion with the protruding portion interposed therebetween and extends in the first direction is provided on a surface of the protruding portion on a side opposite to the support surface, and
  the base substrate is supported on the second wall portion via the second extending portion.

10. The radiation imaging device according to claim 9, wherein the first extending portion and the second extending portion are formed separately from the base substrate.

11. A repair method of the radiation imaging device according to claim 1, the repair method comprising:
  a step of removing a first flexible circuit substrate from the electrode pad in a state in which the radiation detection panel is supported on the base substrate; and
  a step of connecting a second flexible circuit substrate to the electrode pad via the connecting member by heating the connecting member with a first heater disposed on a side opposite to the connecting member with the second flexible circuit substrate interposed therebetween and a second heater disposed on a side opposite to the connecting member with the radiation detection panel interposed therebetween in the state in which the radiation detection panel is supported on the base substrate.

12. The radiation imaging device according to claim 1, wherein the radiation shielding member is made of a material different from a material of the base substrate.

13. The radiation imaging device according to claim 1, wherein the radiation shielding member is spaced apart from the radiation detection panel.

14. The radiation imaging device according to claim 1, wherein the IC chip is disposed between the radiation shielding member and the flexible circuit substrate.

15. The radiation imaging device according to claim 1, further comprising a heat sink member disposed in contact with the IC chip.

16. A method of manufacturing a radiation imaging device, the method comprising:
  a step of preparing a radiation detection panel having a first surface on which a detection region for detecting radiation is formed and an electrode pad is formed outside the detection region, and a second surface on a side opposite to the first surface;
  a step of supporting the second surface of the radiation detection panel on a support surface of a base substrate;
  a step of providing a flexible circuit substrate comprising a first portion and a second portion which is bent to at least partially overlap the first portion when seen in a first direction orthogonal to the support surface, wherein an IC chip is mounted on the second portion of the flexible circuit substrate, and at least a portion of the IC chip is positioned outside of the end portion of the base substrate when seen in the first direction;
  a step of connecting the first portion of the flexible circuit substrate to the electrode pad via a connecting member; and
  a step of providing a radiation shielding member at an edge portion of a back surface of the base substrate opposite to the support surface, wherein a part of the radiation shielding member protrudes to the outside of the base substrate so as to extend between the first portion and the second portion of the flexible circuit substrate and to overlap the IC chip when seen in the first direction,
wherein, in the supporting step, the base substrate is disposed with respect to the radiation detection panel so that an end portion of the base substrate is located further inward than an inner end portion of a connection region in which the electrode pad, the connecting member, and the flexible circuit substrate will overlap each other when seen in the first direction, and
in the connecting step, the connecting member is heated by a first heater disposed on a side opposite to the connecting member with the flexible circuit substrate interposed therebetween and a second heater disposed on a side opposite to the connecting member with the radiation detection panel interposed therebetween.

* * * * *